United States Patent
Flakne et al.

(10) Patent No.: US 10,828,064 B2
(45) Date of Patent: Nov. 10, 2020

(54) LAPAROSCOPIC SIZING INSTRUMENT

(71) Applicants: Torax Medical, Inc., Shoreview, MN (US); Ethicon LLC, Guaynabo, PR (US)

(72) Inventors: Lauren E. Flakne, Cincinnati, OH (US); Michael D. Auld, Blue Ash, OH (US); Brett E. Swensgard, West Chester, OH (US); Kyle P. Taylor, Greenfield, MN (US); Celeste L. Huster, Blaine, MN (US); Jerome K. Grudem, Jr., Rogers, MN (US)

(73) Assignees: Torax Medical, Inc., Shoreview, MN (US); Ethicon LLC, Guaynabo, PR (US)

( * ) Notice: Subject to any disclaimer, the term of this patent is extended or adjusted under 35 U.S.C. 154(b) by 273 days.

(21) Appl. No.: 15/908,875

(22) Filed: Mar. 1, 2018

(65) Prior Publication Data

US 2019/0269436 A1    Sep. 5, 2019

(51) Int. Cl.
*A61B 5/107* (2006.01)
*A61B 17/34* (2006.01)
*A61B 17/29* (2006.01)

(52) U.S. Cl.
CPC ...... *A61B 17/3423* (2013.01); *A61B 17/2909* (2013.01); *A61B 5/107* (2013.01); *A61B 2017/2905* (2013.01); *A61B 2017/345* (2013.01)

(58) Field of Classification Search
CPC ...... A61B 5/107; A61B 5/1076; A61B 5/1073
USPC ............................. 33/512, 555.1, 555.4
See application file for complete search history.

(56) References Cited

U.S. PATENT DOCUMENTS

| | | | | |
|---|---|---|---|---|
| 1,856,295 A | * | 5/1932 | Sovatkin | A61B 5/1076 33/512 |
| 2,241,451 A | * | 5/1941 | Fist | A61B 17/42 600/591 |
| D202,754 S | | 11/1965 | Naftolin et al. | |
| 3,744,140 A | * | 7/1973 | Kyrk | G01B 3/34 33/514.1 |
| D303,010 S | | 8/1989 | Jabbusch | |

(Continued)

OTHER PUBLICATIONS

U.S. Appl. No. 15/664,665, entitled "Method for Assistinga Sphincter," filed Jul. 31, 2017.

(Continued)

*Primary Examiner* — Christopher W Fulton
(74) *Attorney, Agent, or Firm* — Frost Brown Todd LLC

(57) ABSTRACT

An apparatus includes a handle assembly, a shaft assembly, an end effector, and an auto-tensioning feature. The handle assembly includes a body and a plunger. The shaft assembly includes an external sheath that is fixed to the handle body and an interior shaft that is coupled to the plunger. The interior shaft is slidable relative to the external sheath. The end effector is configured to encompass a bodily lumen and includes a flexible member extending distally from the interior shaft. A first coupling element is fixed to the distal tip of the flexible member. A second coupling element is fixed to the external sheath. The first and second coupling elements are magnetically attracted to each other and are biased toward each other such that the flexible member defines an adjustable loop. The auto-tensioning feature is configured to bias the plunger portion proximally relative to the handle body.

20 Claims, 24 Drawing Sheets

(56) References Cited

U.S. PATENT DOCUMENTS

| | | | |
|---|---|---|---|
| 5,171,248 A * | 12/1992 | Ellis | A61B 17/921 33/512 |
| D350,605 S | 9/1994 | Williams | |
| 5,364,365 A | 11/1994 | Wortrich | |
| 5,499,997 A | 3/1996 | Sharpe et al. | |
| D388,171 S | 12/1997 | Fekete | |
| D403,063 S | 12/1998 | Brandhorst et al. | |
| 6,179,791 B1 * | 1/2001 | Krueger | A61B 5/107 33/512 |
| 6,427,351 B1 * | 8/2002 | Matthews | A61B 5/1076 33/512 |
| 6,543,456 B1 | 4/2003 | Freeman | |
| 6,615,504 B2 * | 9/2003 | Oser | A61B 5/107 33/512 |
| 6,695,772 B1 | 2/2004 | Bon et al. | |
| 7,175,589 B2 | 2/2007 | Deem et al. | |
| D561,896 S | 2/2008 | Jones | |
| 7,445,010 B2 | 11/2008 | Kugler et al. | |
| 7,695,427 B2 | 4/2010 | Kugler et al. | |
| 7,824,403 B2 * | 11/2010 | Vaska | A61B 17/2202 33/512 |
| 8,070,670 B2 | 12/2011 | Deem et al. | |
| D667,111 S | 9/2012 | Robinson | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,728,012 B2 * | 5/2014 | Braido | A61B 5/02007 33/512 |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| D828,653 S | 9/2018 | Penland | |
| 2002/0111567 A1 * | 8/2002 | Vanden Hoek | A61B 5/107 600/587 |
| 2006/0253048 A1 | 11/2006 | Jones et al. | |
| 2007/0073098 A1 * | 3/2007 | Lenker | A61B 17/12 600/30 |
| 2011/0098731 A1 | 4/2011 | Whitbrook et al. | |
| 2014/0277421 A1 * | 9/2014 | Conklin | A61F 2/2496 623/2.37 |
| 2018/0161558 A1 | 6/2018 | Penland | |

OTHER PUBLICATIONS

Design U.S. Appl. No. 29/638,804, entitled "Laparoscopic Sizing Instrument," filed Mar. 1, 2018.
Design U.S. Appl. No. 29/638,805, entitled "Laparoscopic Sizing Instrument," filed Mar. 1, 2018.
"FDA Cleard BD's Customizable Micro-Laparoscopic Instruments," Medical Product Outsourcing Magazine, downloaded from Https://www.mpo-mag.com/contents/view_breaking-news/2017-06-20/fda-clears-bds-customizable-micro-laparoscopic-instruments, 2017, 7 pgs.

* cited by examiner

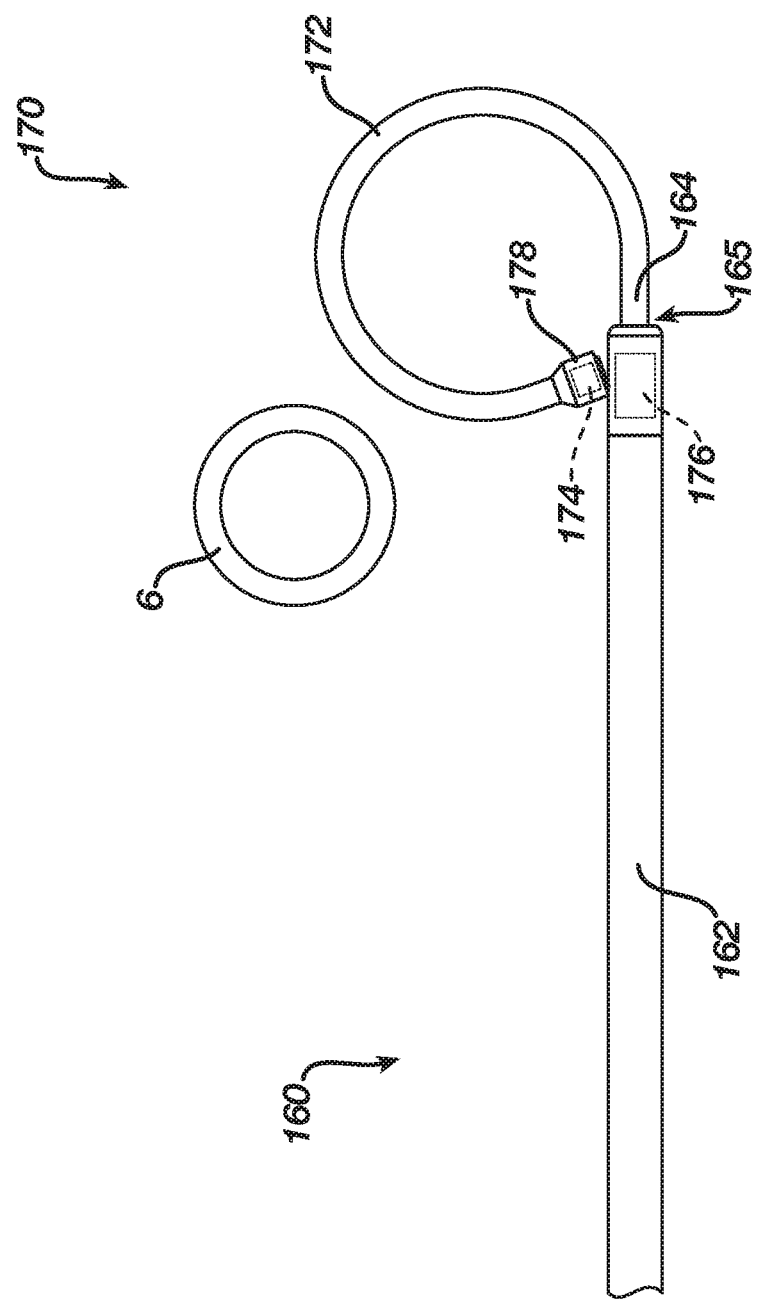

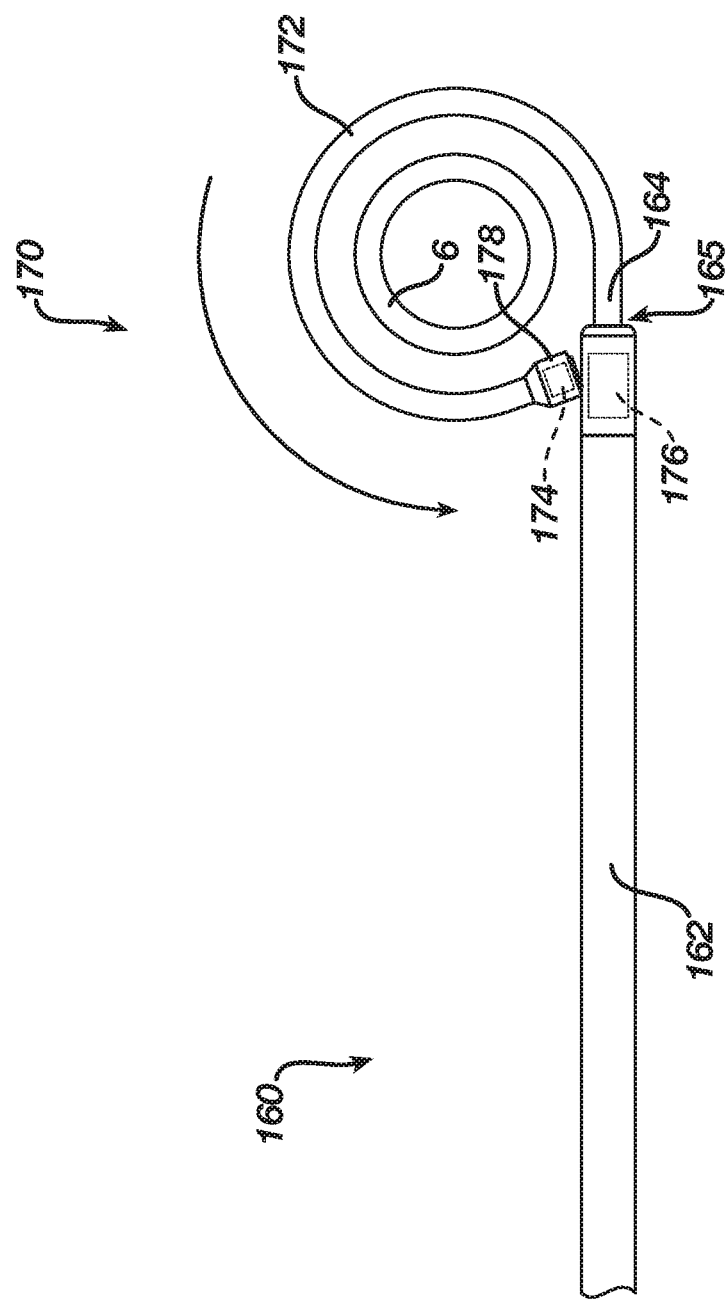

LAPAROSCOPIC SIZING INSTRUMENT

FIELD OF THE INVENTION

The invention pertains to laparoscopic sizing instruments. More specifically, the invention pertains to laparoscopic sizing instruments for a biological lumen and/or passageway.

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease (or "GERD"), which effects the esophagus.

A normal, heathy, esophagus is a muscular tube that carries food from the mouth, through the chest cavity and into the upper part of the stomach. A small-valved opening in the esophagus, called the lower esophageal sphincter (or "LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

SUMMARY OF THE INVENTION

An apparatus is used to encompass a bodily lumen. The apparatus includes a handle assembly, a shaft assembly, and end effector, and an auto-tensioning feature. The handle assembly includes a handle body and a plunger portion slidably coupled with the handle body. The shaft assembly extends distally from the handle assembly. The shaft assembly includes an external sheath fixed to the handle body, and an interior shaft coupled to the plunger portion. The interior shaft is slidable relative to the external sheath. The end effector is configured to encompass the bodily lumen. The end effector includes a flexible member, a first coupling element, and a second coupling element. The flexible member includes a distal tip and extends distally form the interior shaft. The first coupling element is fixed to the distal tip of the flexible member. The second coupling element is fixed to the external sheath. The first and second coupling elements are biased toward each other such that the flexible member defines an adjustable loop. The auto-tensioning feature is configured to bias the plunger portion proximally relative to the handle body.

An apparatus is used to encompass a bodily lumen. The apparatus includes a handle assembly, a shaft assembly, and end effector, and an auto-tensioning feature. The handle assembly includes a handle body and a plunger portion slidably coupled with the handle body. The shaft assembly extends distally from the handle assembly. The shaft assembly includes an external sheath fixed to the handle body, and an interior shaft coupled to the plunger portion. The interior shaft is slidable relative to the external sheath. The end effector is configured to encompass the bodily lumen. The end effector includes a flexible member, which includes a distal tip. The flexible member extends distally from the interior shaft. The flexible member is biased to define an adjustable loop. The auto-tensioning feature is position within the external sheath and around the interior shaft. The auto-tensioning feature is configured to bias the plunger portion proximally relative to the handle body to reduce the adjustable loop defined by the flexible member.

An apparatus is used to encompass a bodily lumen. The apparatus includes a handle assembly, a shaft assembly, and end effector, and an auto-tensioning feature. The handle assembly includes a static body and an actuating slidably coupled with the static body. The shaft assembly extends distally from the handle assembly. The shaft assembly includes an external sheath fixed to the static body, and an interior shaft coupled to the actuating body. The external sheath defines a distal opening. The end effector is configured to encompass the bodily lumen. The end effector includes a flexible member attached to the interior shaft. A distal portion of the flexible member extends distally past the distal opening of the external sheath. The distal portion of the flexible member is biased to form an adjustable loop.

The auto-tensioning feature is configured to bias the actuating body portion proximally relative to the static body.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18A depicts a top plan view of the end effector and shaft assembly of FIG. 7 placed adjacent to a lower esophageal sphincter, where the end effector is in a distal, closed, position;

FIG. 18C depicts a top plan view of the end effector and shaft assembly of FIG. 7, where the end effector is in the distal, closed, position while the end effector surrounds the lower esophageal sphincter;

Figure 1:
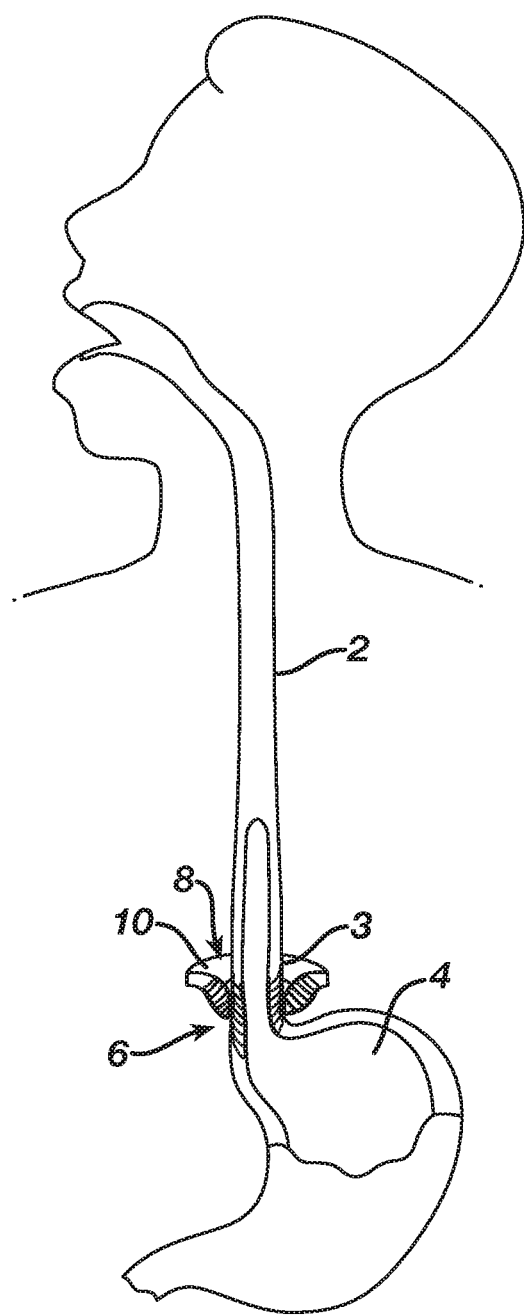
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview

Figure 2:
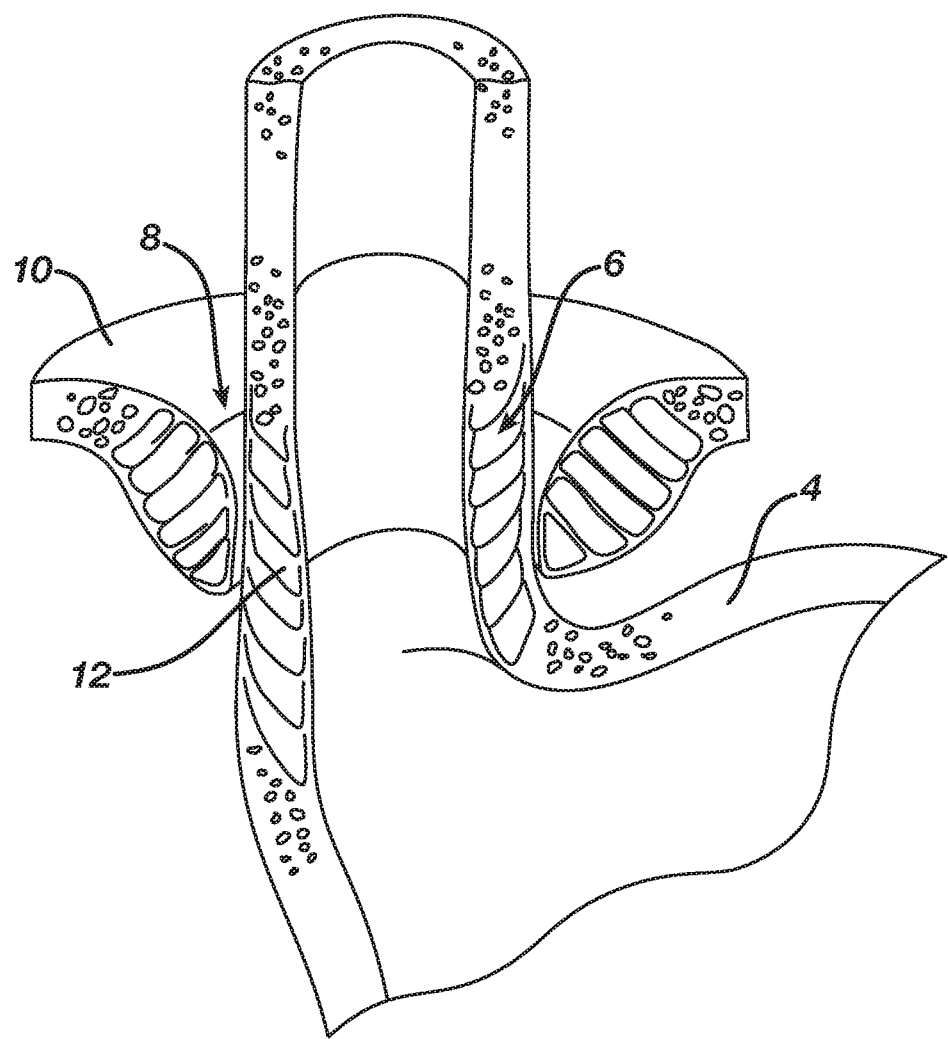
FIG. 2 depicts a cross-sectional isometric view, taken along a coronal plane of the body, of a human esophagogastric junction.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state in order to act as a valve. In other words, a healthy LES (6) may transition from the occluded state to the opened state in order to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

If LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant around a malfunctioning LES (6) such that the implant and/or LES (6) may properly transition between the occluded state and the opened state.

Such an implant may include a circumferential array of magnetic elements that are magnetically attracted toward adjacent magnetic elements. Such magnetic elements may expand and contract relative to each other while encompassing the exterior of a malfunctioning LES (6). Therefore, the magnetic attraction between adjacent magnetic elements may help a malfunction LES (6) properly remain in an occluded state; while the ability for magnetic elements to expand and contract relative to each other may allow an LES (6) to suitably transition into the opened state. While magnetic elements are used to bias a malfunctioning LES (6) toward an occluded state while also allowing a malfunctioning LES (6) to suitably transition into an open state, any other type of biasing elements may be used as would be apparent to one having ordinary skill in the art in view of the teachings herein. Merely illustrative examples of implants that may be used to encompass the exterior of a malfunctioning LES (6) are disclosed in U.S. Pat. No. 7,695,427, the disclosure of which is incorporated by reference herein and U.S. patent application Ser. No. 15/664,665, entitled "Method for Assisting a Sphincter," filed Jul. 31, 2017 issued as U.S. Pat. No. 10,405,865 on Sep. 10, 2019, the disclosure of which is incorporated by reference herein.

II. Exemplary Laparoscopic Sizing Instrument

As mentioned above, certain implants may encompass a malfunctioning LES (6) within the body to suitably assist such sphincters in properly transitioning between the occluded state and the open state. Since the diameter of the LES (6) may vary from patient to patient, it may be necessary or otherwise desirable to vary the length of an implant, to correspond with the diameter of the LES (6) of the patient at hand, to thereby maximize the likelihood of a successful outcome. The suitable length of an implant (i.e. circumference of an implant when attached to the outer diameter of LES (6)) may be determined by measuring the outer diameter of the LES (6) of the patient at hand. For instance, if an implant includes an array of magnetic elements, the number of magnetic elements used for a specific implant may be determined by the outer diameter of LES (6). The larger the outer diameter, the more magnetic elements will be used; and the smaller the outer diameter, the less magnetic elements will be used.

Since the outer diameter of LES (6) may vary depending on the patient, and this may influence the configuration of an implant that is to be placed around the LES (6), it may be desirable to use a sizing instrument having an end effector that is configured to encompass and measure an outer diameter of an LES (6) of an individual patient. An operator may utilize the measurement of LES (6) to determine what size implant should be used for an individual patient. Upon identifying the appropriate size of the implant, the operator may select the appropriately sized implant from a plurality of available implants. Alternatively, the operator may modify the length of an implant to achieve the appropriate size.

Additionally, in some instances, it may be desirable to provide a sizing instrument with an auto-tensioning feature that is configured to drive the end effector of a sizing instrument into proper engagement with the outer diameter of LES (6). An auto-tensioning feature may prevent an operator from manually driving an end effector too far into engagement with the outer diameter of LES (6) such that end effector no longer suitably encompasses LES (6) for an accurate measurement of LES (6), or such that the hollow organ deforms. An auto-tensioning feature may also prevent an operator from manually driving an end effector too loose such that the end effector does not properly engage the outer diameter of LES (6). If an operator manually drives an end effector too far or too loose into engagement with the outer diameter of LES (6), this may ultimately provide an inaccurate measurement of the outer diameter of LES (6), which may lead to using an implant having an improper length. Using an implant having improper length (i.e., too long) may prevent implant of assisting LES (6) in appropriately closing. Additionally, using an implant having improper length (i.e., too short) may lead to potential dysphagia or erosion into tissue where the implant may be too tight.

The following describes an exemplary laparoscopic sizing instrument (100) having an auto-tensioning feature (166) that may be utilized to provide a proper engagement between an end effector (170) of sizing instrument (100) and the outer diameter of LES (6). While sizing instrument (100) is described herein in the context of measuring the LES (6) of esophagus (2), variations of sizing instrument (100) may be used to measure the outer circumference of any other anatomical passageway, including but not limited to the pylorus, the intestinal region surrounding the ileocecal sphincter, a passageway associated with the sphincter of Oddi, a region of a urethra surrounding the urethral sphincter, a region of the rectum, a region surrounding the upper esophageal sphincter, or any other anatomical passageway.

Figure 3:
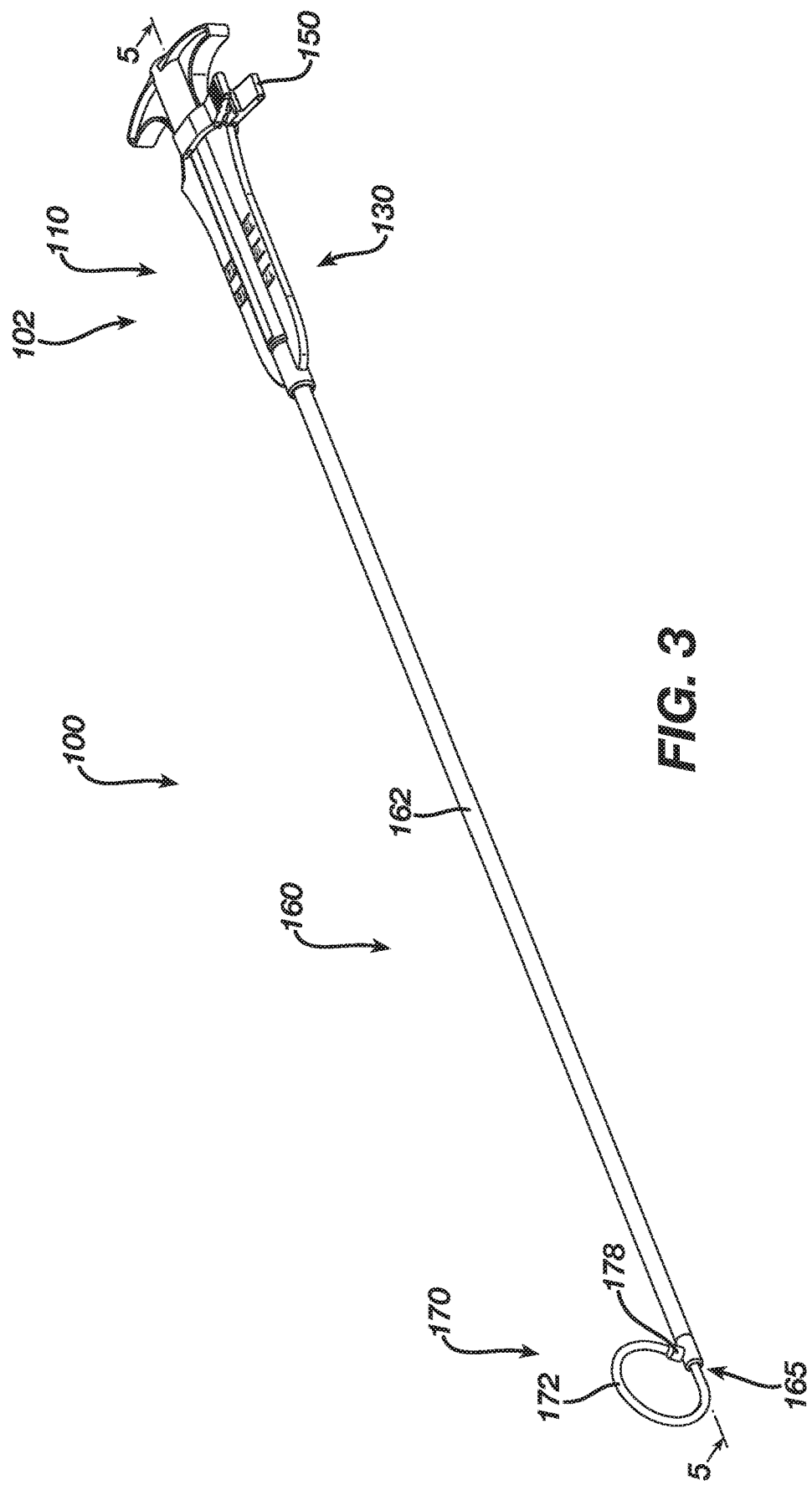
FIG. 3 depicts a perspective view of an exemplary laparoscopic sizing instrument that may be used to measure the biological passage of FIG. 1.
Figure 4:
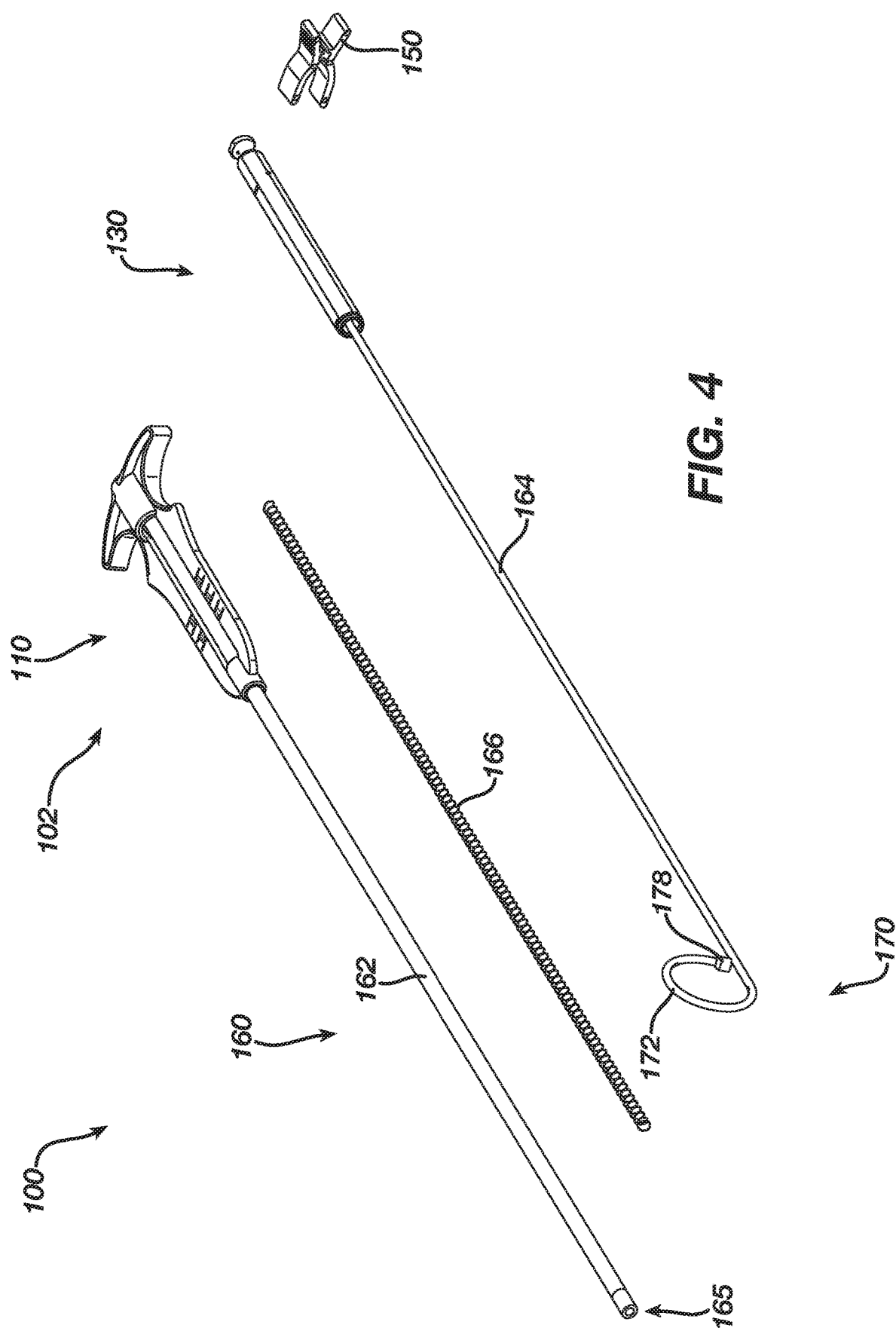
FIG. 4 depicts an exploded perspective view of the laparoscopic sizing instrument of FIG. 3.

As shown in FIGS. 3-4, sizing instrument (100) of the present example includes a handle assembly (102), a shaft assembly (160) extending distally from handle assembly (102), and an end effector (170) extending distally from handle assembly (102). Handle assembly (102) includes a grip portion (110), a plunger portion (130), and a locking clip (150). Shaft assembly (160) includes an exterior sheath (162), a translating interior shaft (164) slidably housed within exterior sheath (162), and auto-tensioning feature (166) housed within exterior sheath (162) and around a portion of interior shaft (164). End effector (170) includes a resilient flexible tube (172) extending distally from translating interior shaft (164), a first magnet (174) attached to a distal tip (178) of resilient flexible tube (172), and a second magnet (176) located at an open distal end (165) of exterior sheath (162). While second magnet (176) is not shown in FIGS. 3-4, second magnet (176) is shown in FIGS. 7, 11, and 18A-18D. In some variations, distal end (165) of exterior sheath (162) simply includes a ferrous cuff or other ferrous element that is configured to magnetically couple with first magnet (174); instead of including second magnet (176).

Resilient flexible tube (172) defines an adjustable loop, and is resiliently biased to assume the loop configuration shown in FIGS. 3-4. While the current example includes resilient flexible tube (172), any other type of elongated resilient flexible member may be used as would be apparent to one having ordinary skill in the art in view of the teachings herein.

Figure 18B:
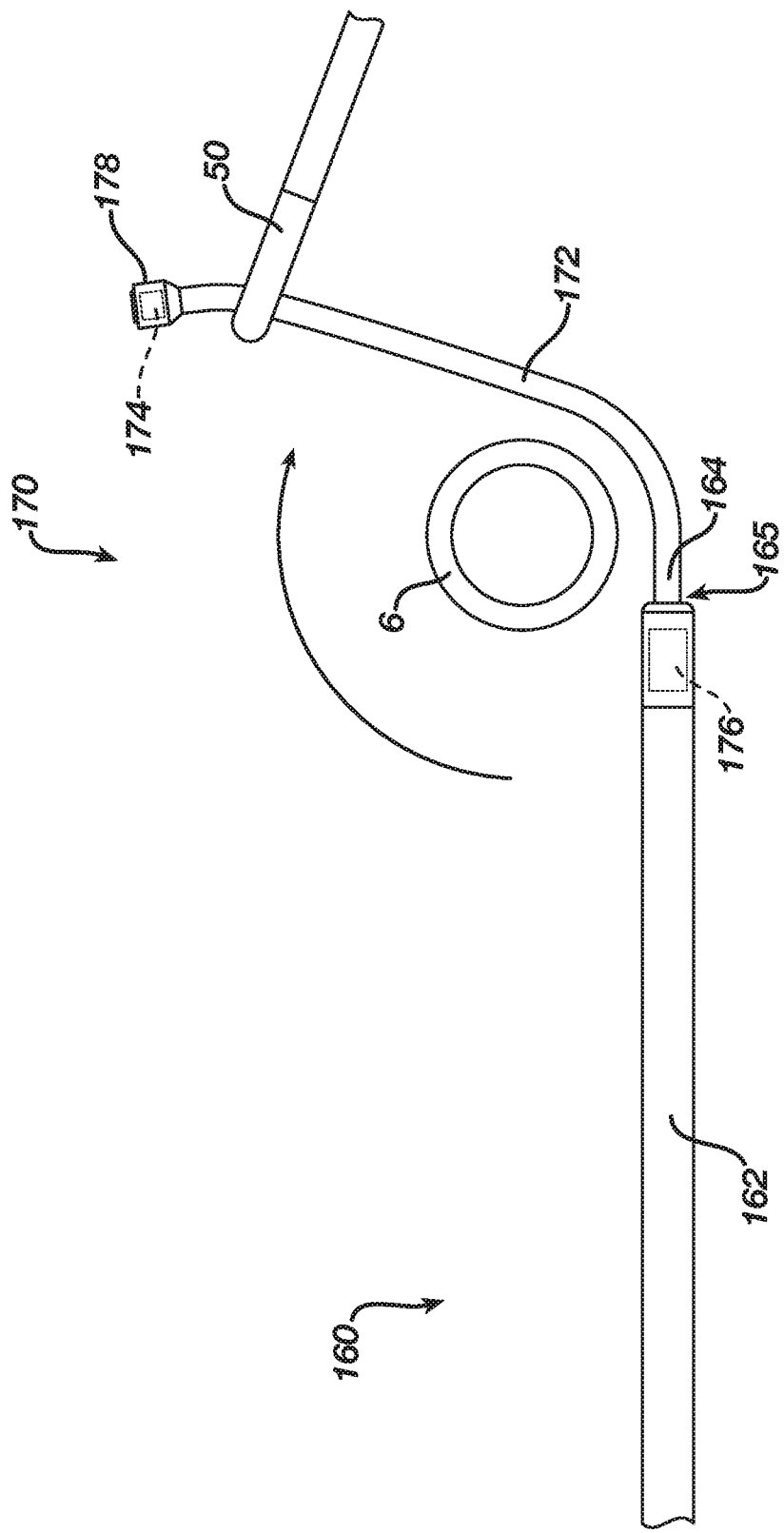
FIG. 18B depicts a top plan view of the end effector and shaft assembly of FIG. 7 placed adjacent to the lower esophageal sphincter, where the end effector is in a distal, opened, position.
Figure 18D:
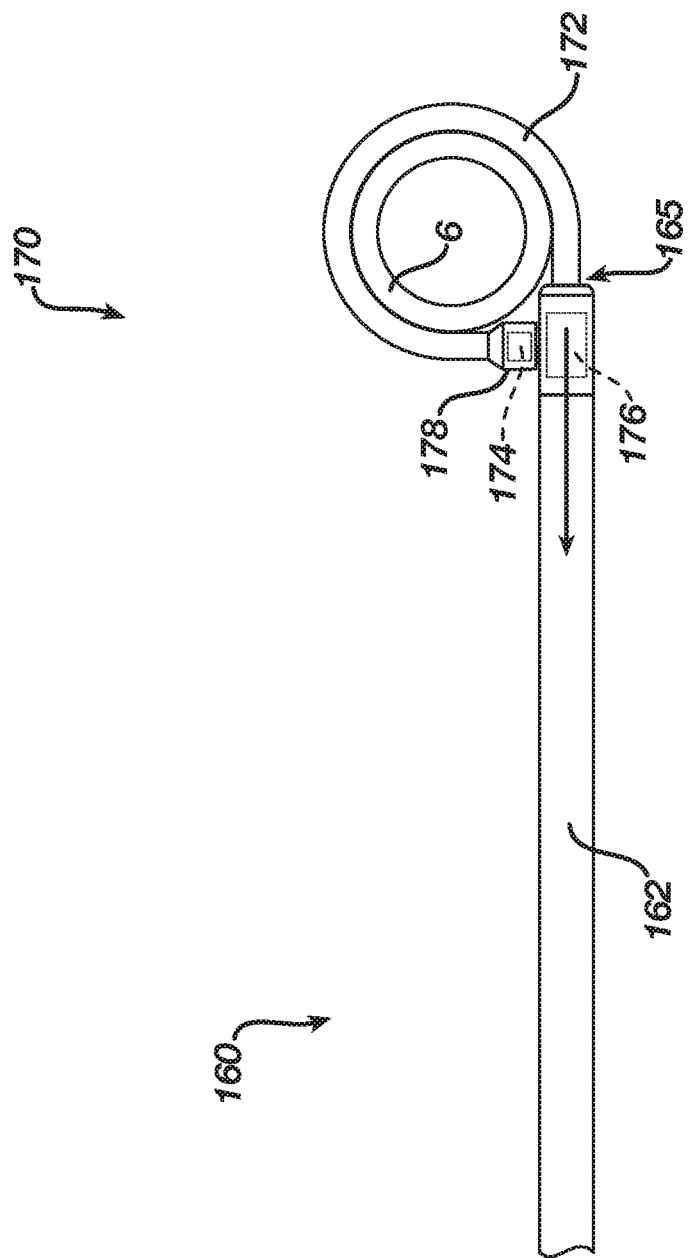
FIG. 18D depicts a top plan view of the end effector and shaft assembly of FIG. 7, where the end effector is in a retracted, closed, position while the end effector surrounds the lower esophageal sphincter.

As will be described in greater detail below, resilient flexible tube (172) is configured to transition between a closed position (as shown in FIGS. 18A and 18C) and an opened position (as shown in FIG. 18B) in order to selectively encompass LES (6). As will also be described in greater detail below, auto-tensioning feature (166) is configured to decrease the diameter of the adjustable loop defined by resilient flexible tube (172) until resilient flexible tube (172) sufficiently engages the outer diameter of LES (6) (as shown in FIG. 18D).

Figure 8:
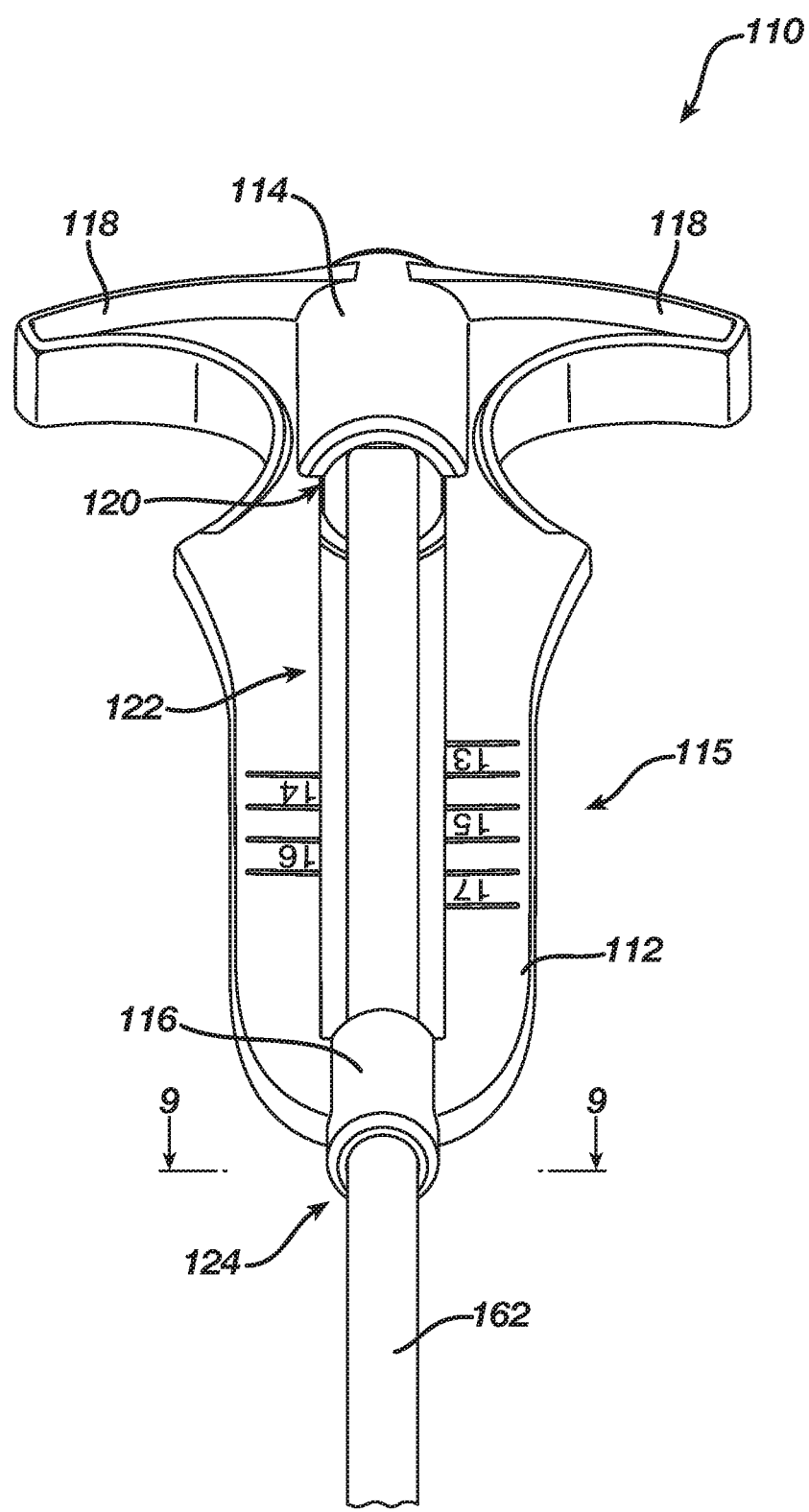
FIG. 8 depicts a perspective view of a grip portion of the handle assembly of FIG. 5.
Figure 9:
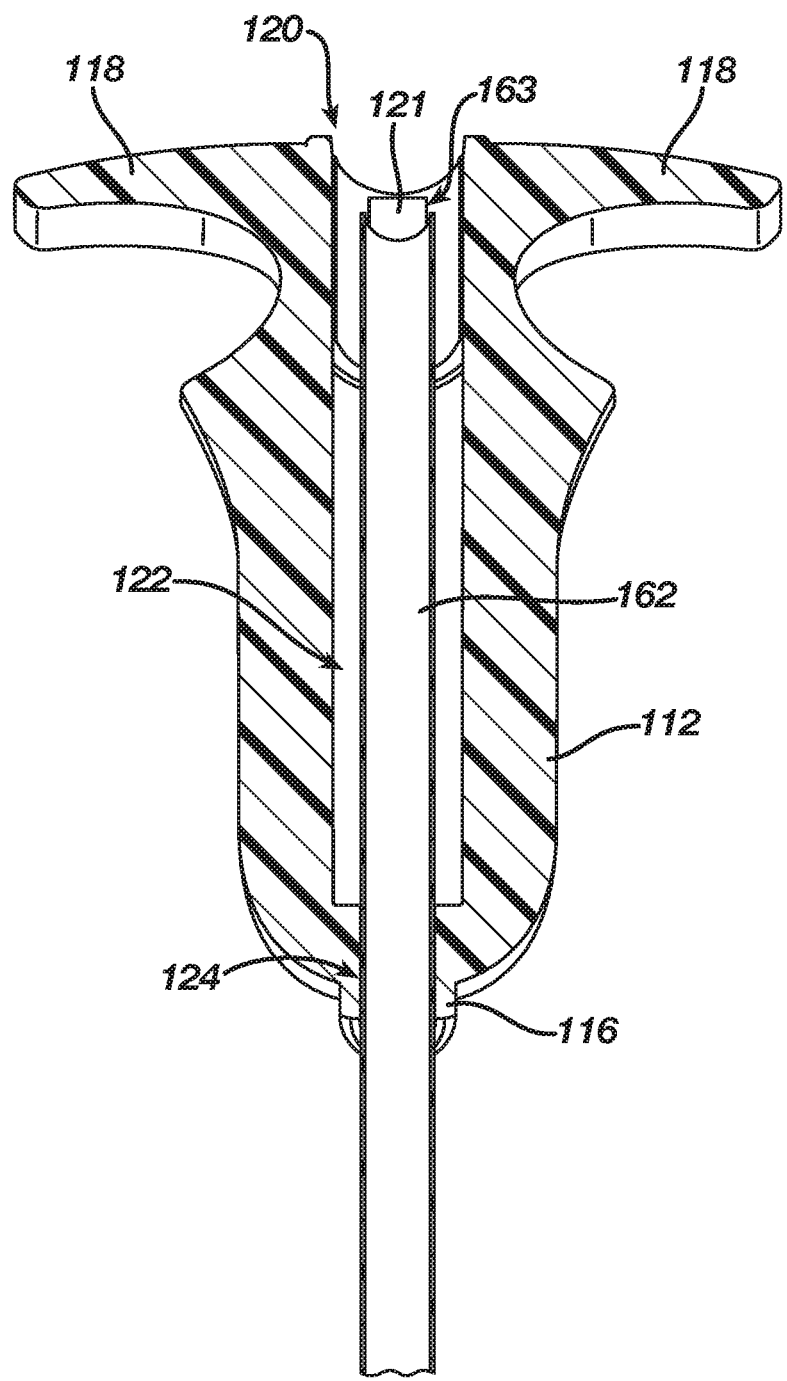
FIG. 9 depicts a cross sectional perspective view of the grip portion of FIG. 8, taken along line 9-9 of FIG. 8.

As best seen in FIGS. 8-9, grip portion (110) of handle assembly (102) includes an elongated body (112) extending from a proximal sleeve (114) toward a distal locking collar (116). Grip portion (110) also includes a pair of finger grips (118) extending laterally from proximal sleeve (114). Finger grips (118) may allow an operator to better grasp grip portion (110) during exemplary use. Elongated body (112) includes a plurality of indicator markings (115). Indicator markings (115) are dimensioned to correspond with an indicator (146) on plunger portion (130) when end effector (170) sufficiently engages the outer diameter of LES (6), thereby indicating the suitable size of implant to be used in conjunction with LES (6). In the present example, indicator markings (115) have a series of sections ranging between 13 and 17, where each number corresponds with a specific sized implant. For example, if indicator (146) on plunger portion (130) is aligned within the range associated with "15" when end effector (170) sufficiently engages the outer diameter of LES (6), a corresponding size "15" implant may be used in conjunction with the recently measured LES (6). While indicator markings (115) in the current example ranges between 13 and 17, any suitable range may be used as would be apparent to one having ordinary skill in the art in view of the teachings herein. Additionally, any suitable unit may be used as would be apparent having ordinary skill in the art in view of the teachings herein. For example, millimeters may be the identified unit.

Proximal sleeve (114) defines a sleeve channel (120), elongated body (112) defines a plunger window (122), and distal locking collar (116) defines a collar channel (124). Collar channel (124), plunger window (122), and sleeve channel (120) are dimensioned to receive exterior sheath (162); while distal locking collar (116) couples with exterior sheath (162) of shaft assembly (160) such that exterior sheath (162) and grip portion (110) are fixed relative to each other. Plunger window (122) and sleeve channel (120) are dimensioned to slidably receive plunger portion (130) such that plunger portion (130) may translate relative to grip portion (110). Additionally, as will be described in greater detail below, the proximal portion of exterior sheath (162) is housed within plunger window (122) and sleeve channel (120) such that exterior sheath (162) may slidably support plunger portion (130) during exemplary use. As best seen in FIG. 9, an open proximal end (163) of exterior sheath (162) is housed within sleeve channel (120) of proximal sleeve (114). However, this is merely optional, as open proximal end (163) may be located at any other suitable position as would be apparent to one having ordinary skill in the art in view of the teachings herein.

Figure 7:
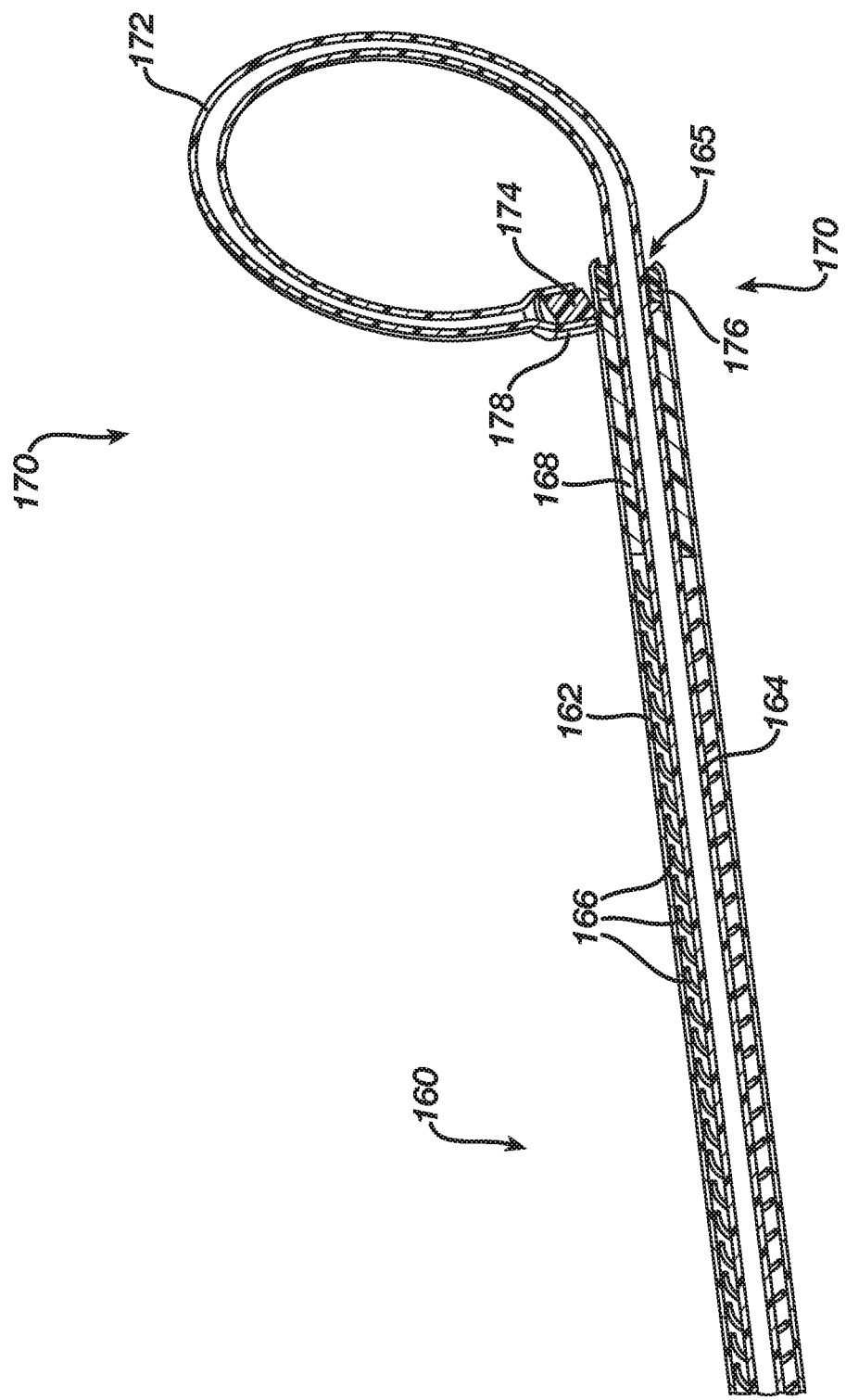
FIG. 7 depicts a cross-sectional perspective view of a shaft assembly and end effector of the laparoscopic sizing instrument of FIG. 3, taken along line 5-5 of FIG. 3.
Figure 10:
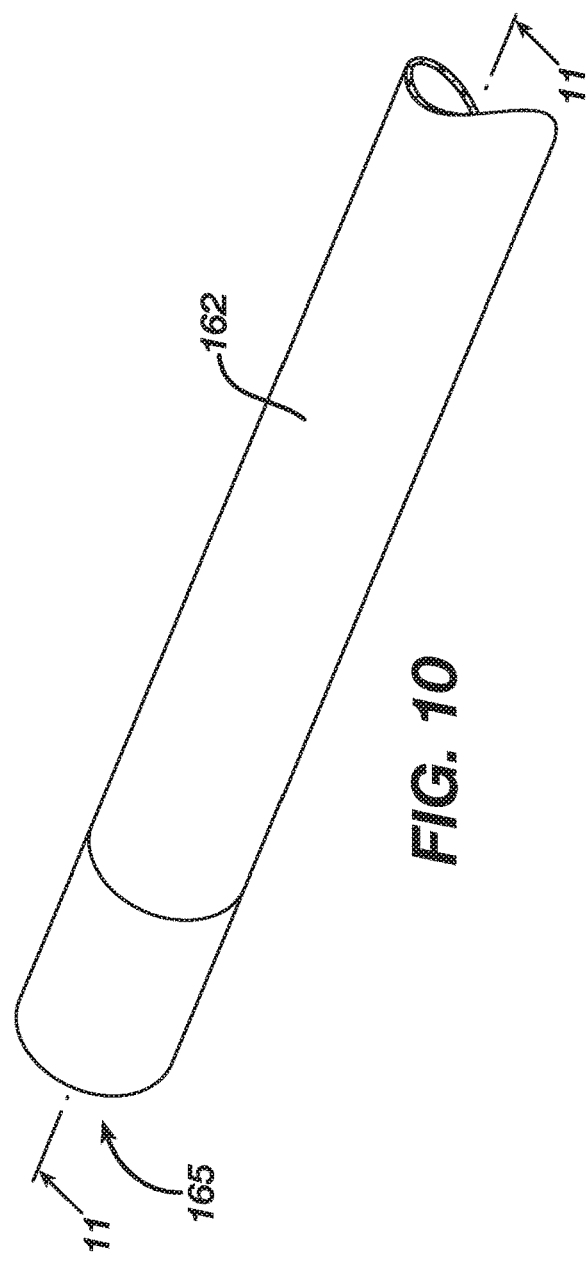
FIG. 10 depicts a perspective view of a distal end of an exterior sheath of the shaft assembly of FIG. 7.
Figure 11:
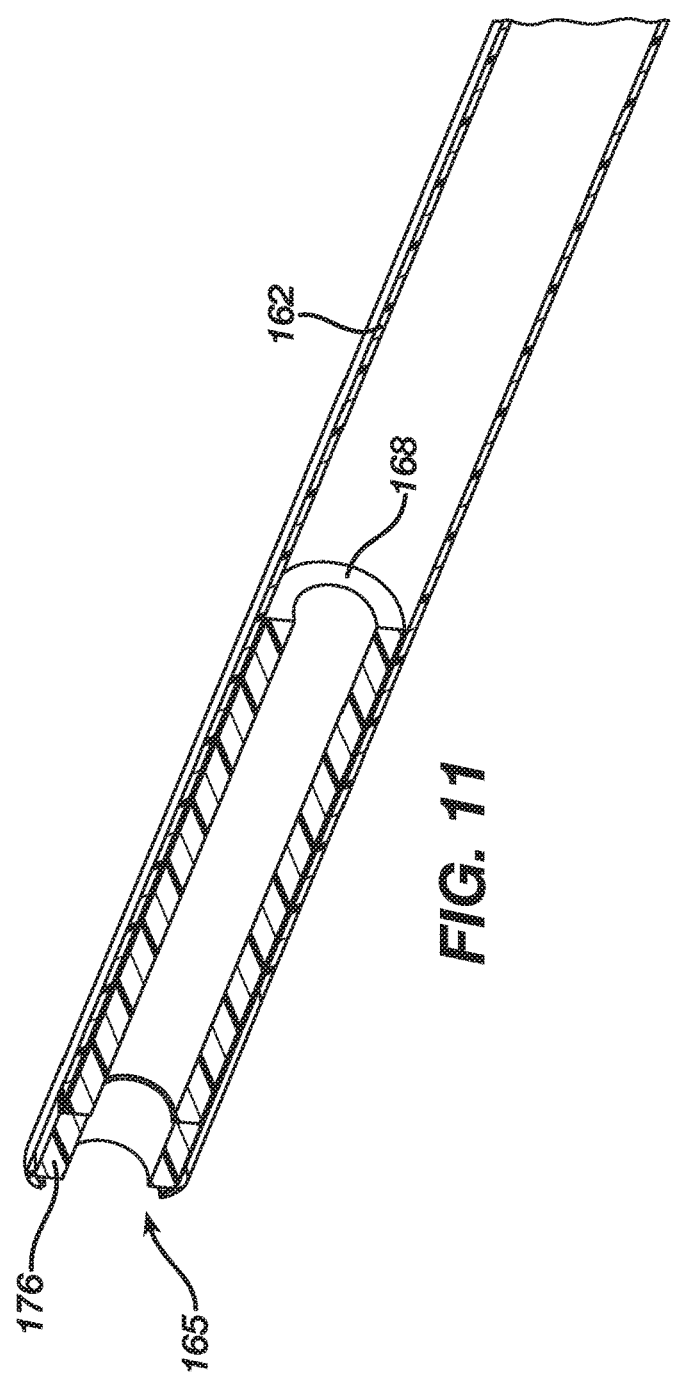
FIG. 11 depicts a cross-sectional perspective view of the distal end of the exterior sheath of FIG. 10, taken along line 11-11 of FIG. 10.

As best seen in FIG. 7 and FIGS. 10-11, the distal portion of exterior sheath (162) houses a spacer tube (168) and second magnet (176). Spacer tube (168) and second magnet (176) are both fixed within in the interior of sheath (162). As best shown in FIG. 7, spacer tube (168) is configured to abut against a distal end of auto-tensioning feature (166), thereby acting as a mechanical ground for auto-tensioning feature (166).

Figure 12:
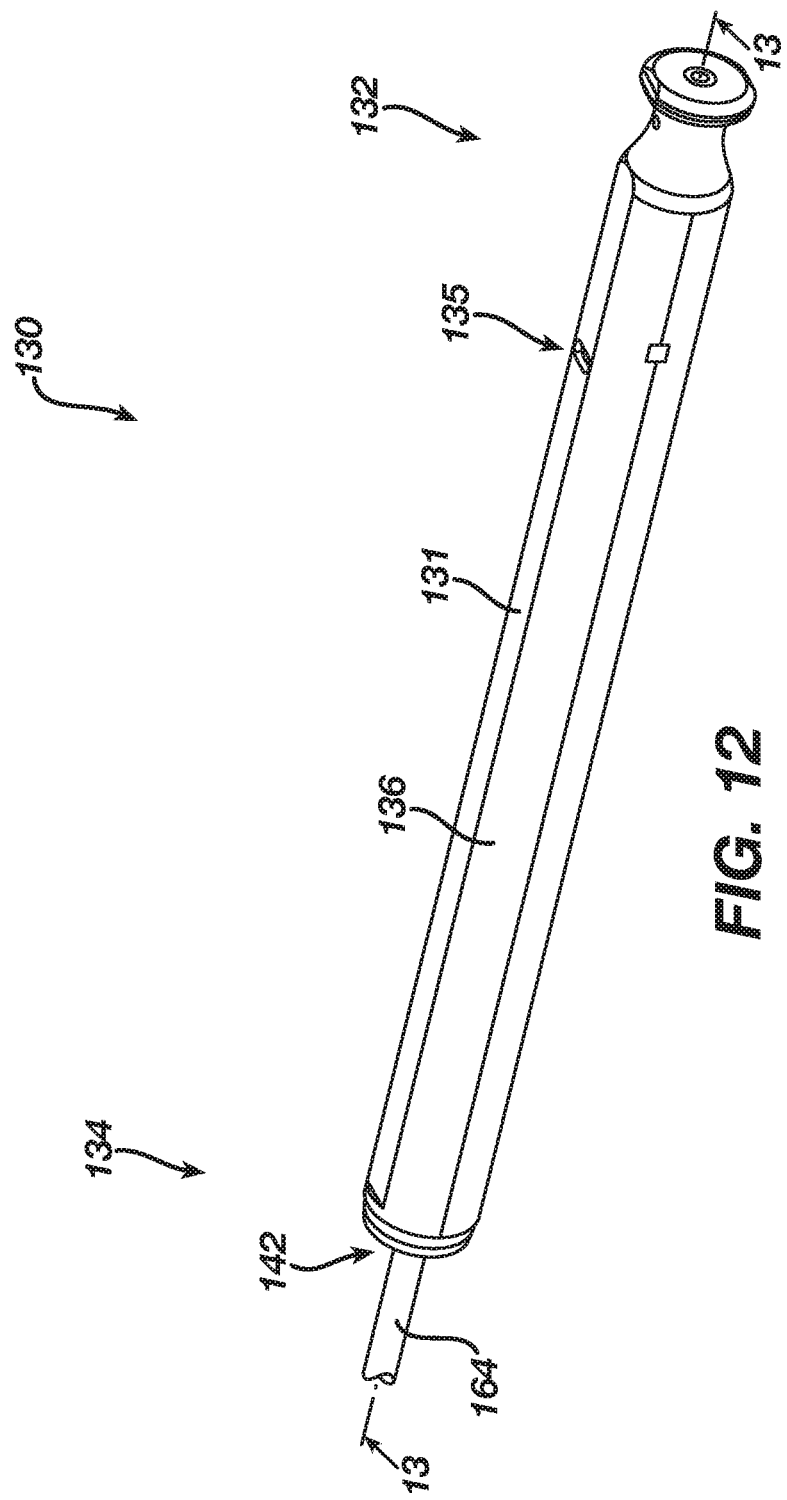
FIG. 12 depicts a perspective view of a plunger portion of the handle assembly of FIG. 5.
Figure 13:
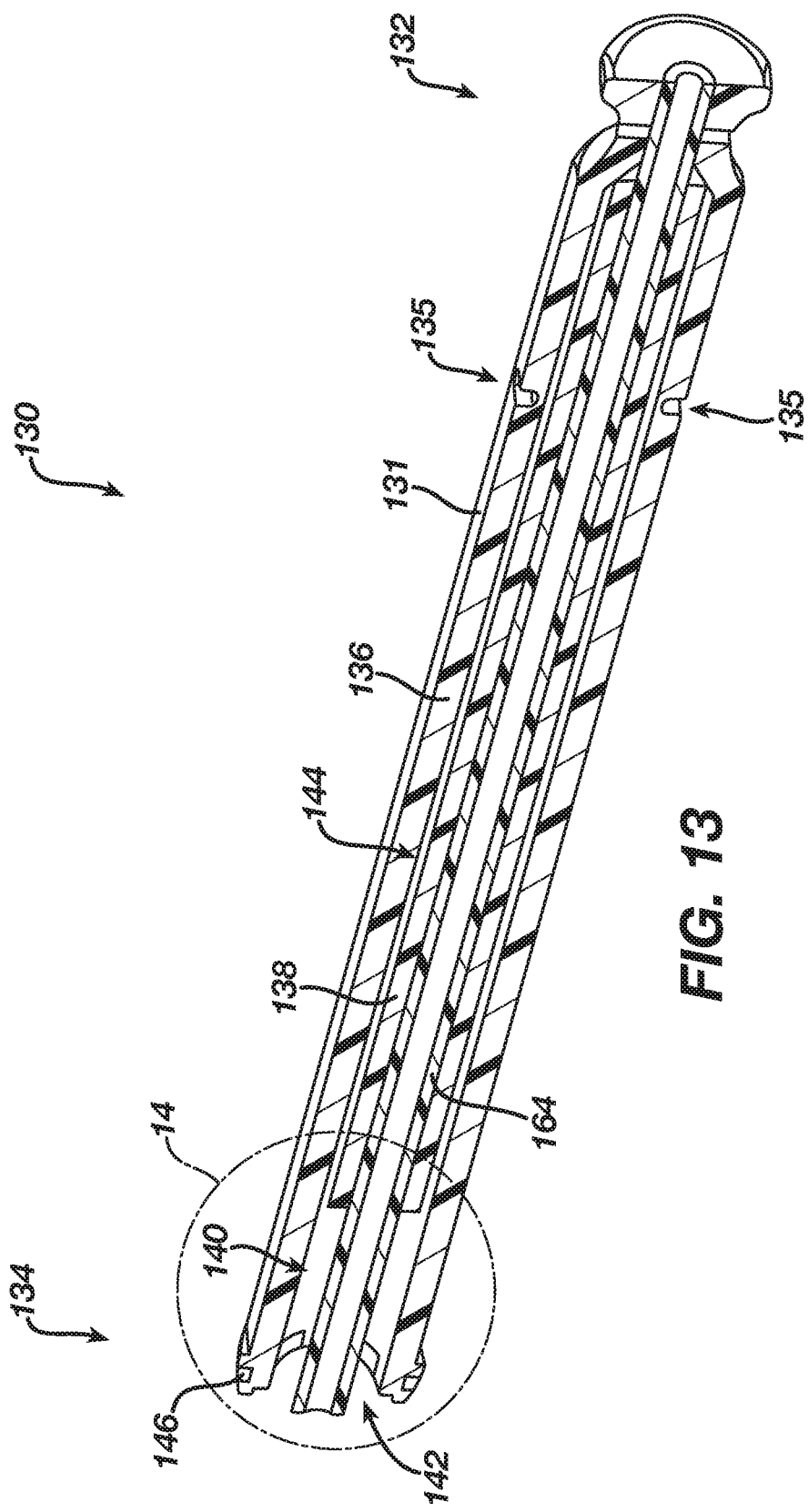
FIG. 13 depicts a cross-sectional perspective view of the plunger portion of FIG. 12, taken along line 13-13 of FIG. 12.
Figure 14:
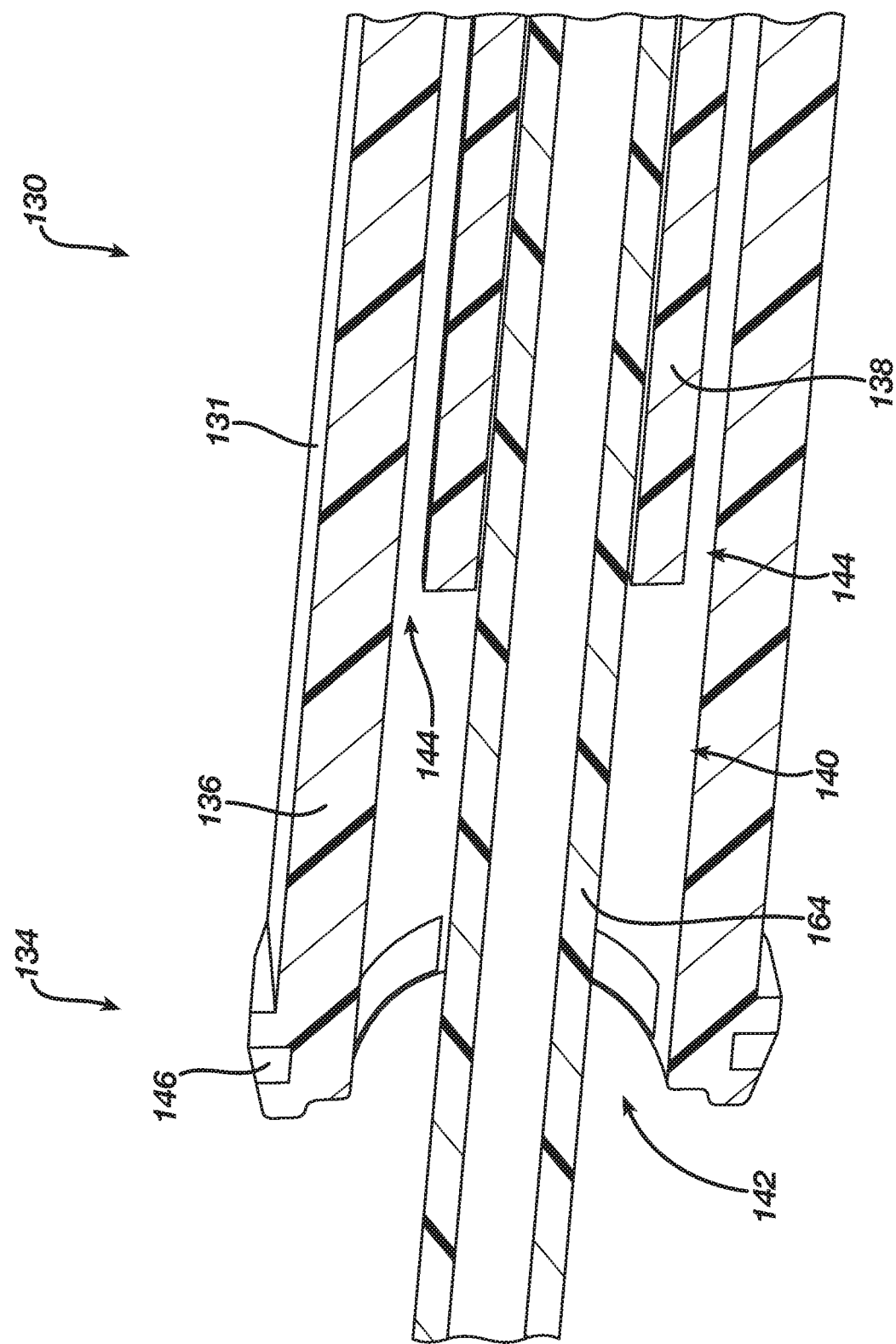
FIG. 14 depicts an enlarged cross-sectional perspective view of the plunger portion shown in FIG. 13, taken along line 13-13 of FIG. 12.
Figure 15:
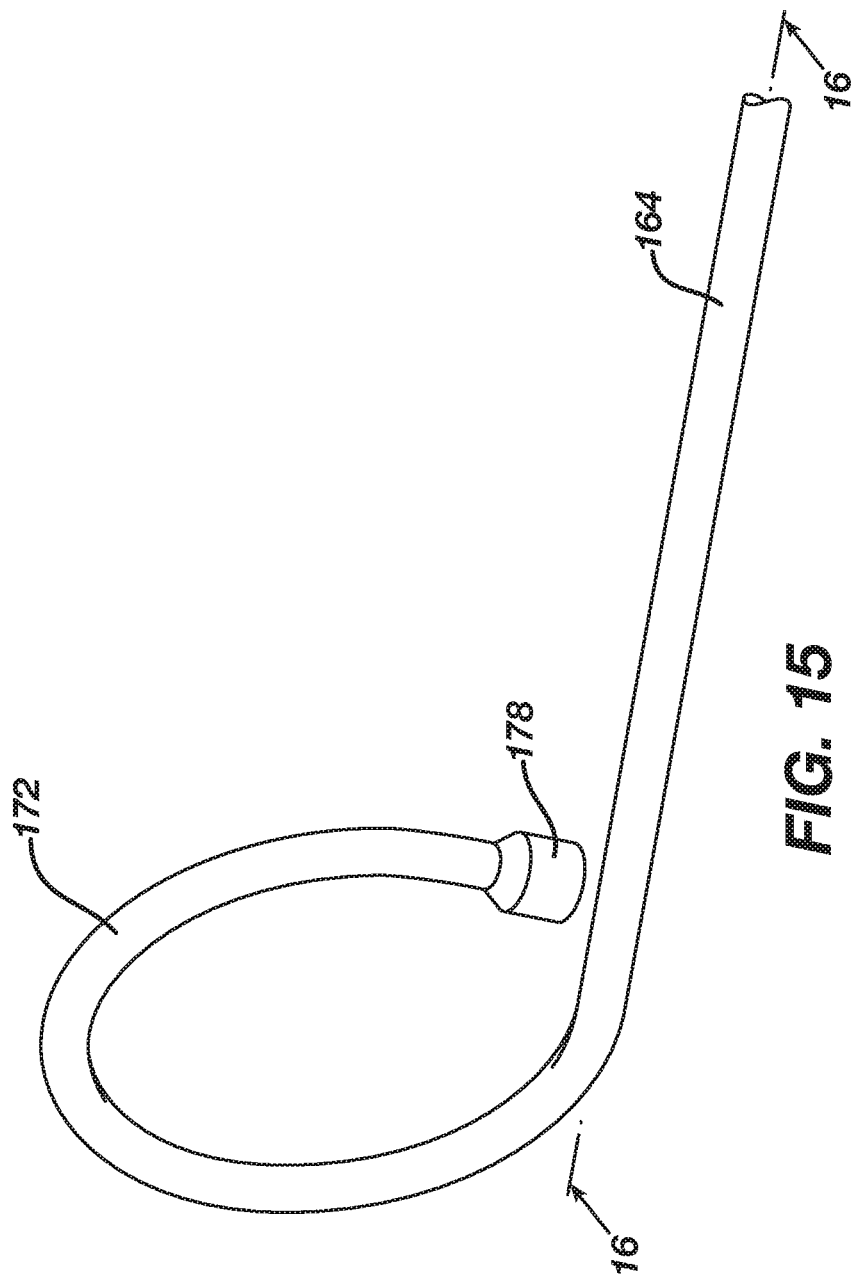
FIG. 15 depicts a perspective view of the translating interior shaft of the shaft assembly of FIG. 7.
Figure 16:
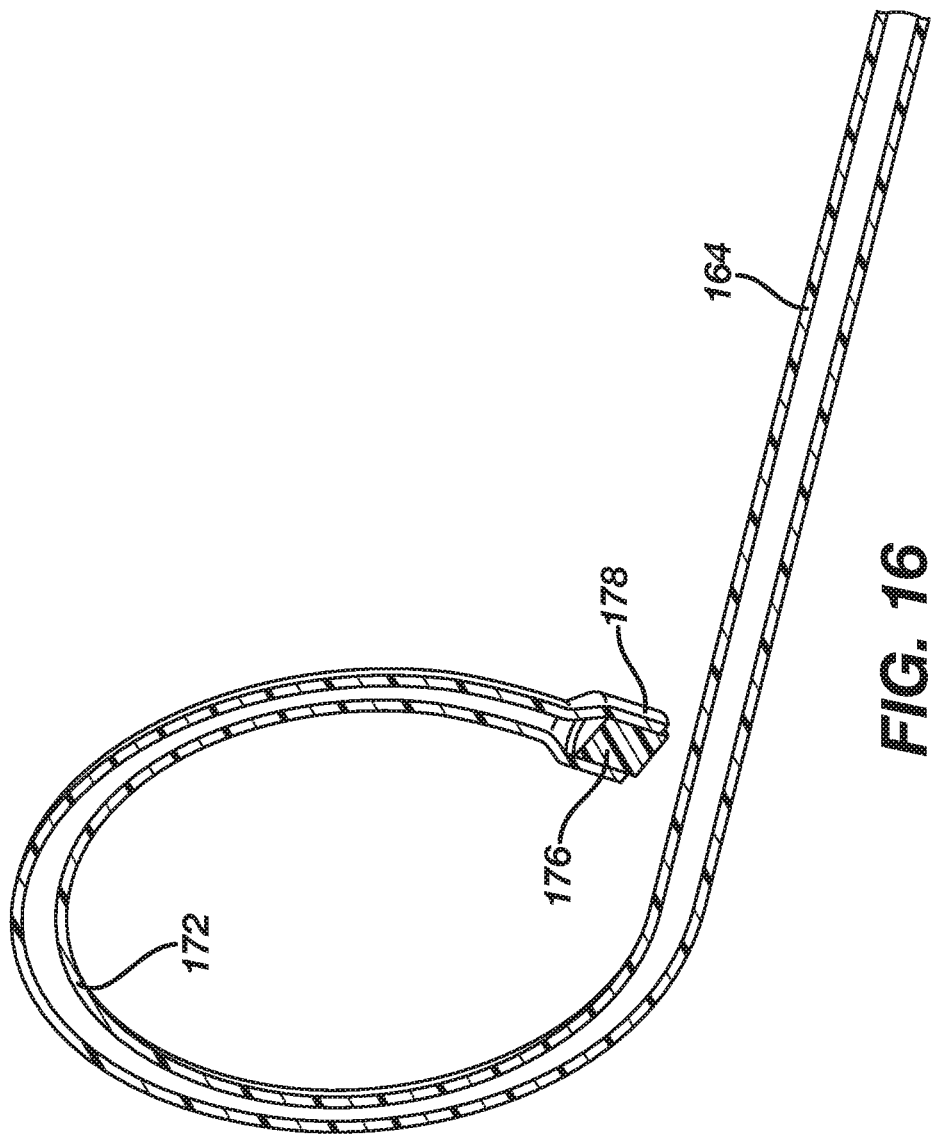
FIG. 16 depicts a cross-sectional perspective view of the translating interior shaft of FIG. 15, taken along line 16-16 of FIG. 15.
Figure 17:
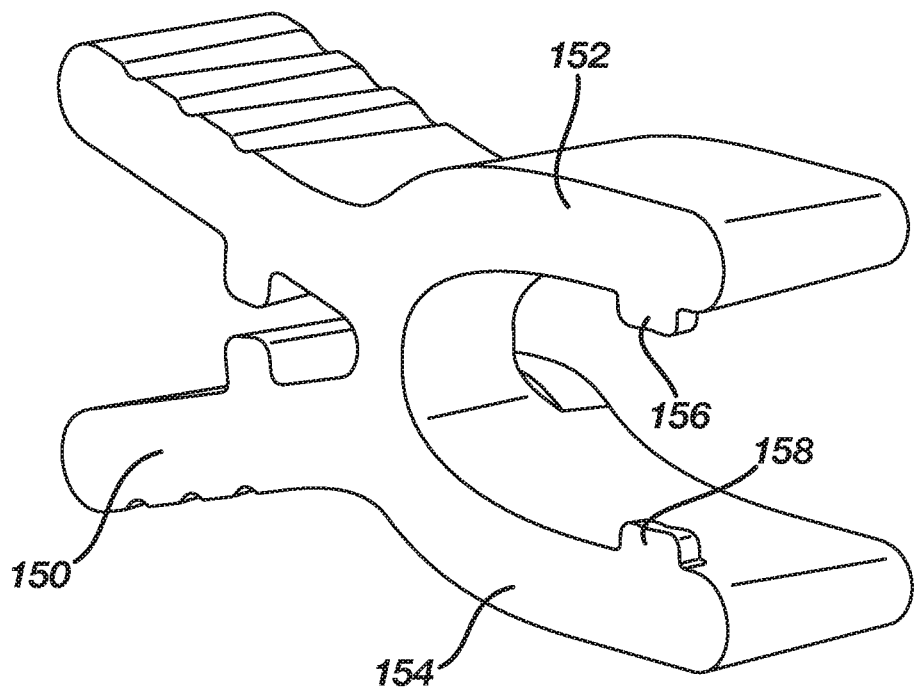
FIG. 17 depicts a perspective view of a locking clip of the laparoscopic sizing instrument of FIG. 3.
Figure 20A:
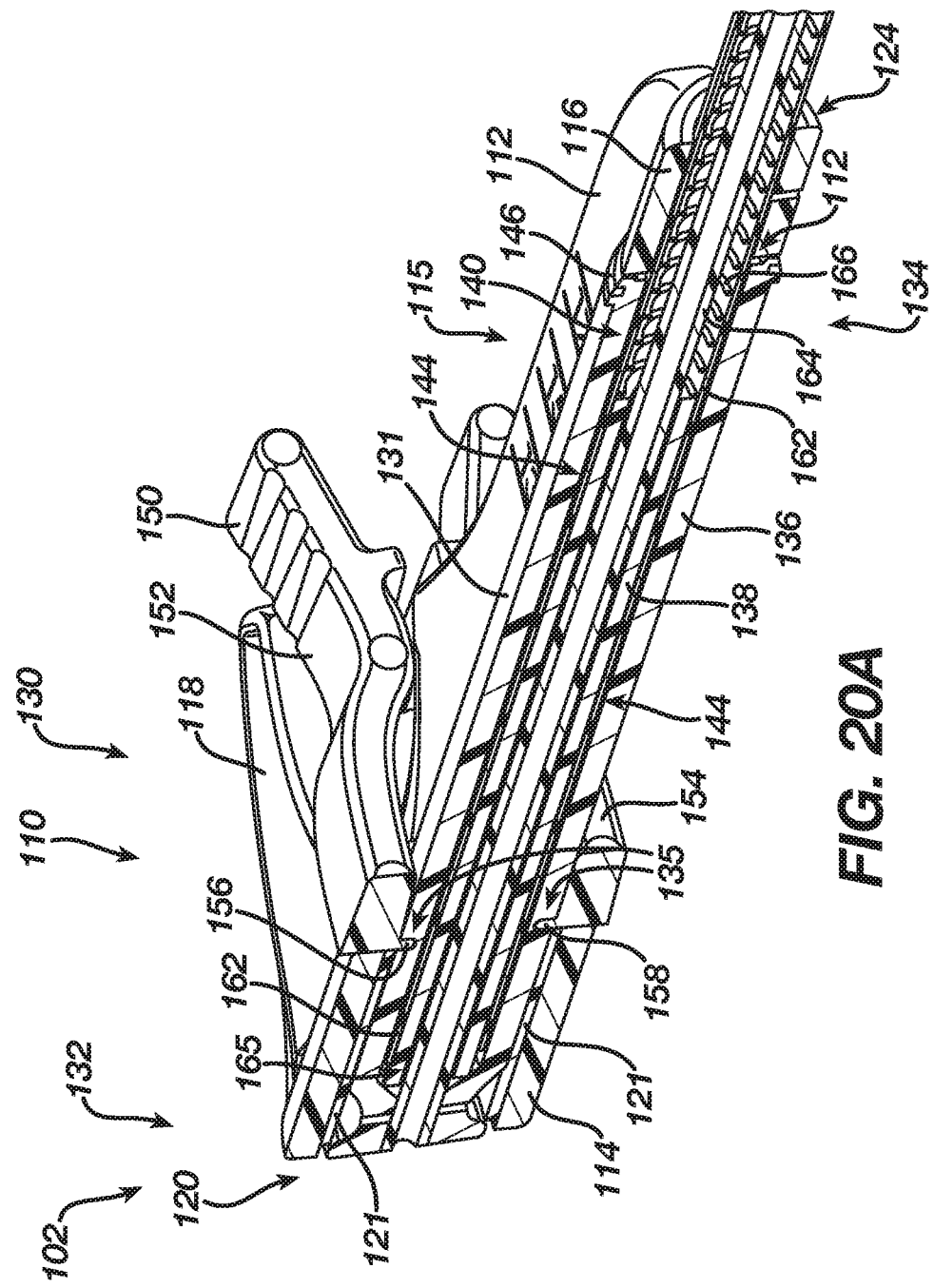
FIG. 20A depicts a cross-sectional perspective view of the handle assembly of FIG. 5, where the plunger portion of FIG. 12 is in a distal position corresponding with the end effector in the distal, closed, position.
Figure 20B:
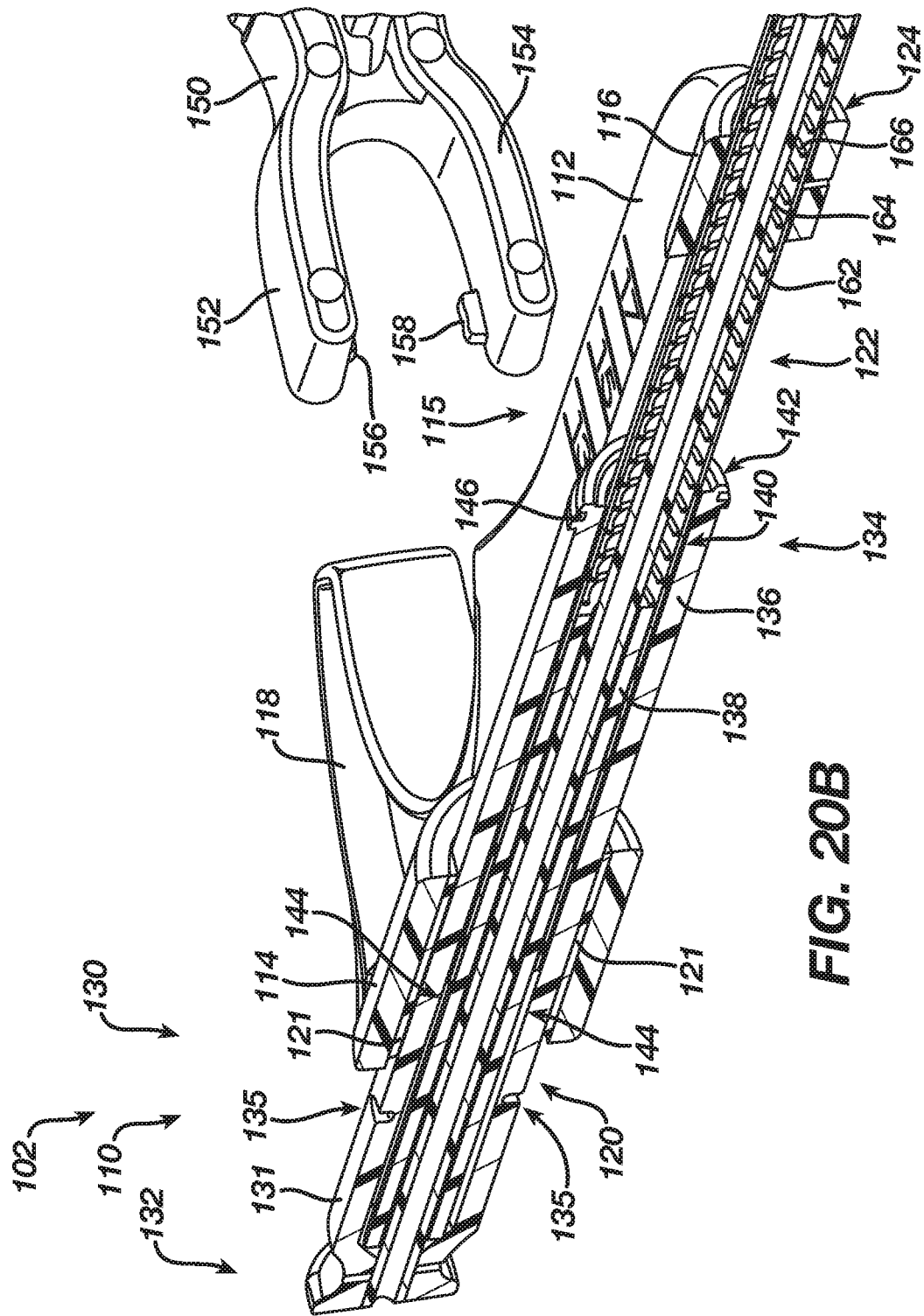
FIG. 20B depicts a cross-sectional perspective view of the handle assembly of FIG. 5, where the plunger portion of FIG. 12 is in a proximal position corresponding with the end effector in the retracted, closed, position.

FIGS. 12-14 show plunger portion (130) of handle assembly (102). Plunger portion (130) extends from a proximal portion (132) to a distal portion (134). As mentioned above, plunger portion (130) is slidably housed within sleeve channel (120) and plunger window (122) of grip portion (110). Plunger portion (130) includes external plunger body (136) defining a cavity (140) extending into a distal opening (142); and a support collar (138) housed within cavity (140). External plunger body (136) includes indicator (146) and a pair of flats (131). As best seen in FIGS. 20A-20B, flats (131) are dimensioned to abut against flats (121) of proximal sleeve (114) such that external plunger body (136) may not rotate relative to grip portion (110). Therefore, plunger portion (130) may translate relative to grip portion (110), but plunger portion (130) may not rotate about its own longitudinal axis relative to grip portion (110).

External plunger body (136) also defines a pair of locking recesses (135). As will be described in greater detail below, locking recesses (135) are configured to engage a locking clip (150) while plunger portion (130) is in a distal position such that plunger portion (130) is longitudinally fixed relative to grip portion (110) while simultaneously compressing auto-tensioning feature (166). As will be described in greater detail below, locking clip (150) may be removed from plunger portion (130) such that auto-tensioning feature (166) may proximally drive plunger portion (130) relative to grip portion (110).

Figure 5:
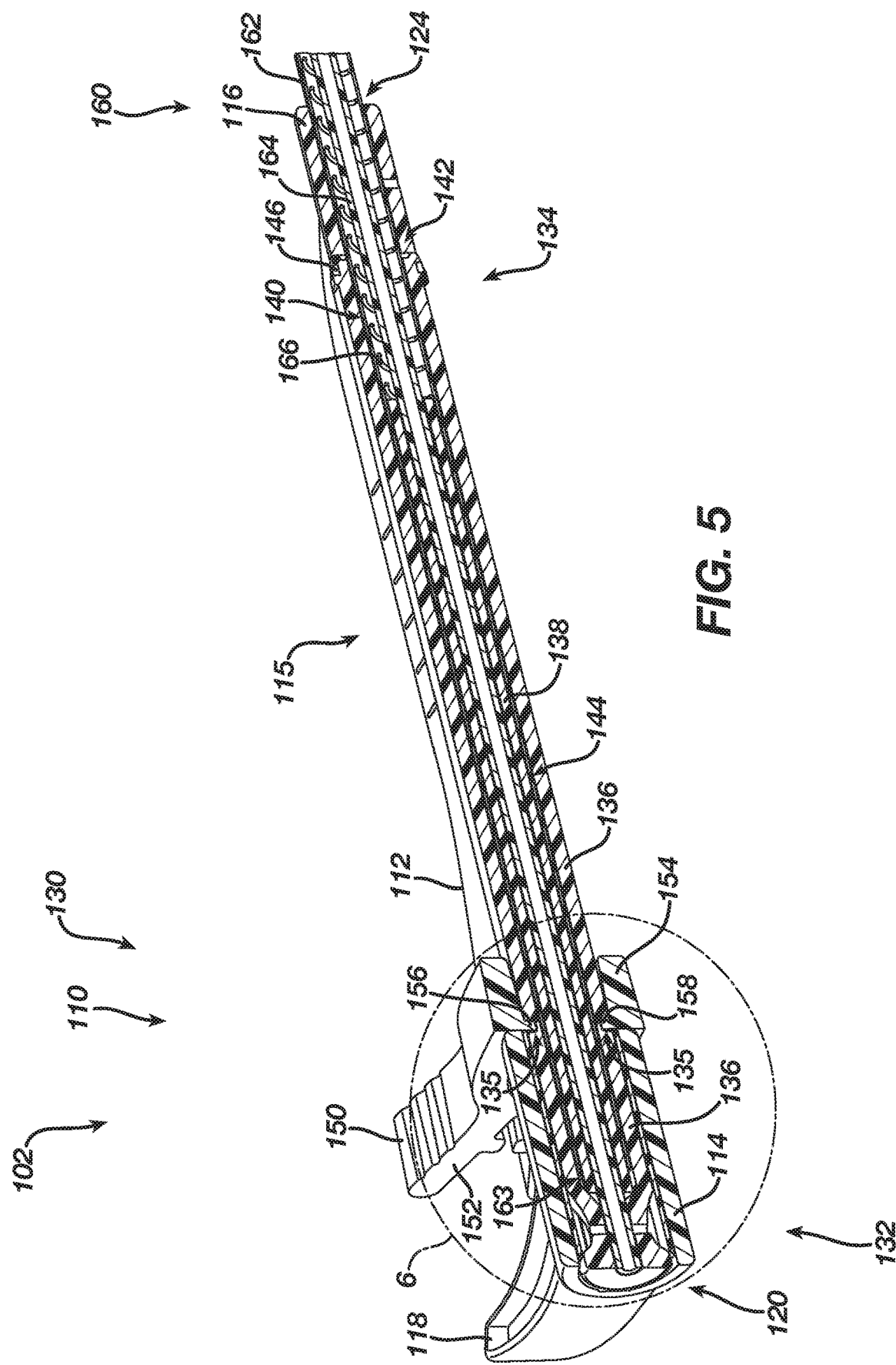
FIG. 5 depicts a cross-sectional perspective view of a handle assembly of the laparoscopic sizing instrument of FIG. 3, taken along line 5-5 of FIG. 3.
Figure 6:
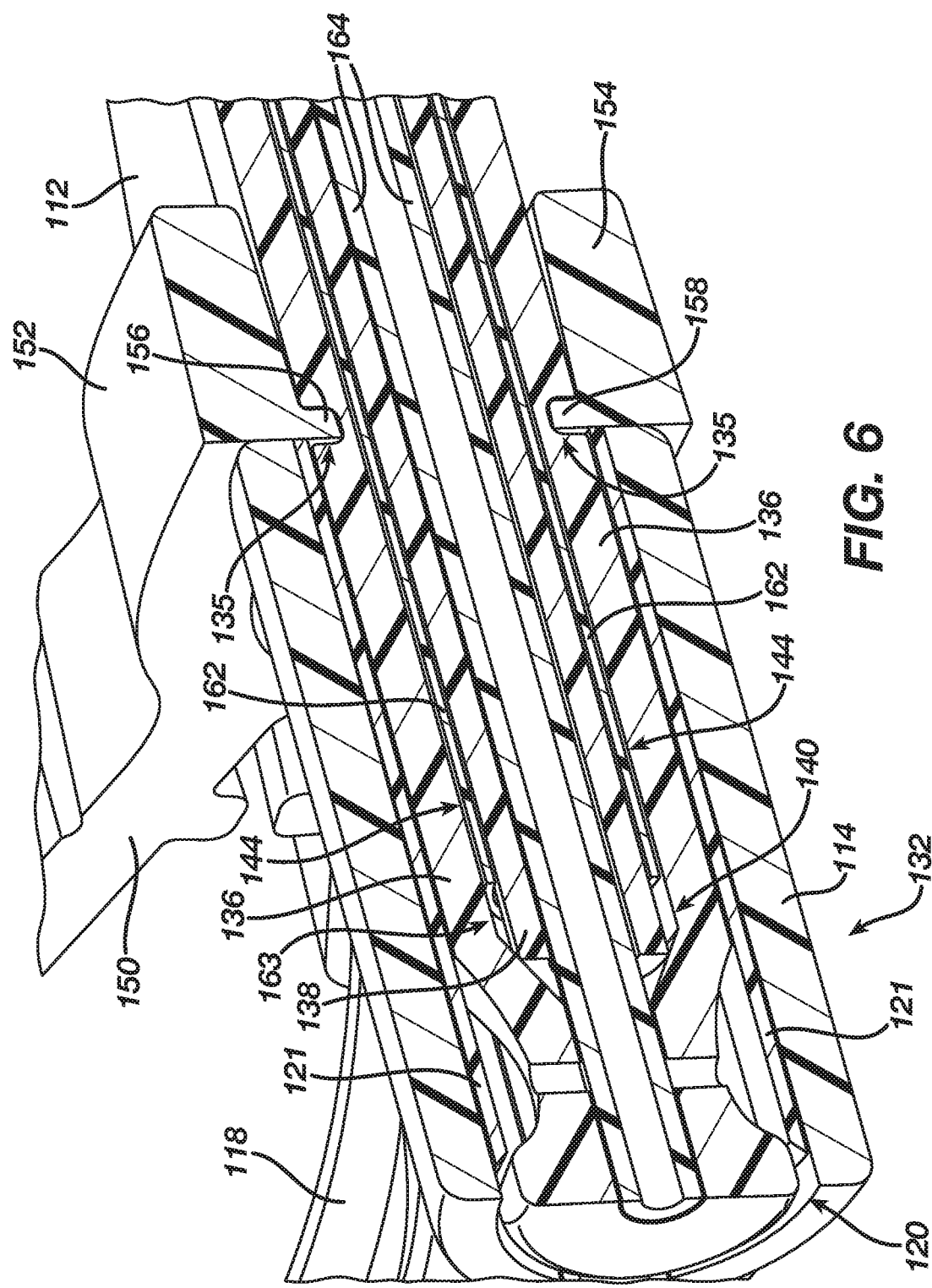
FIG. 6 depicts an enlarged cross-sectional perspective view of the handle assembly shown in FIG. 5, taken along line 5-5 of FIG. 3.

As best seen in FIGS. 5-6 and FIG. 13, support collar (138) is fixed to a proximal end of translating interior shaft (164). Additionally, support collar (138) is fixed to external plunger body (136). Therefore, interior shaft (164) may actuate with plunger portion (130) relative to grip portion (110) and exterior sheath (162). As best seen in FIG. 5 and FIGS. 20A-20B, an external surface of support collar (138) and an interior surface of external plunger body (136) define a slide gap (144). As mentioned above, exterior sheath (162) may slidably support plunger portion (130) during exemplary use. In the present example, slide gap (144) is dimensioned to slidably receive the proximal portion of exterior sheath (162) located within plunger window (122) and sleeve channel (120) such that exterior sheath (162) may slidably support plunger portion (130). In other words, proximal opening (142) and cavity (140) of external plunger body (136) slidably receives exterior sheath (162), while a portion of support collar (138) is slidably housed within exterior sheath (162).

As mentioned above, and as best seen in FIG. 7, end effector (170) includes resilient flexible tube (172), first magnet (174) associated with distal tip (178) of resilient flexible tube (172), and second magnet (176) associated with open distal end (165) of exterior sheath (162). Resilient flexible tube (172) is biased toward a closed position (as shown in FIG. 7). Resilient flexible tube (172) is configured to flex from the closed position (as shown in FIG. 18A) to an opened position (as shown in FIG. 18B) in response to an external force. Resilient flexible tube (172) is also resiliently biased to flex back from the opened position to the closed position (as shown in FIG. 18C) after an external force is no longer acting on resilient flexible tube (172). In other words, flexible tube (172) may flex such that distal tip (178) of tube (172) does not make contact with open distal end (165) of exterior sheath (162), thereby "opening" the tube (172). Resilient flexible tube (172) may include a leaf spring to bias itself toward the closed position. Alternatively, resilient flexible tube (172) may be biased to the position shown in FIG. 7 by any suitable means as would be apparent to one having ordinary skill in the art in view of the teachings herein. For instance, resilient flexible tube (172) may be constructed of a shape memory material.

As also mentioned above, resilient flexible tube (172) is coupled to a distal end of translating interior shaft (164), which is coupled to plunger portion (130). Therefore, resilient flexible tube (172) may actuate relative to exterior sheath (162) in response to movement of plunger portion (130). As shown between FIGS. 18C-18D, movement of resilient flexible tube (172) relative to exterior sheath (162) affects the dimension of the loop defined by resilient flexible tube (172). In particular, the loop defined by tube (172) may become larger in response to distal translation of plunger portion (130); while the loop defined by tube (172) may become smaller in response to proximal translation of plunger portion (130). Therefore, the loop defined resilient flexible tube (172) is largest when plunger portion (130) is in the most distal position. The size of the loop defined by resilient flexible tube (172) may be determined from the longitudinal position of indicator (146) on plunger portion (130) relative to indicator markings (115) on grip portion (110).

First and second magnets (174, 176) are attracted to each other such that distal tip (178) of resilient flexible tube (172) is biased toward engagement with open distal end (165) of exterior sheath (162). As noted above, second magnet (176) may be replaced with a ferrous element (e.g., metallic cuff, etc.) in some variations. In the present example, first and second magnets (175, 176) may help ensure that distal tip (178) of resilient flexible tube (172) maintains contact with open distal end (165) of exterior sheath (162) even after the loop defined by resilient flexible tube (172) decreases in diameter. In other words, first and second magnets (174, 176) may help ensure resilient flexible tube (172) remains in a closed position as the loop defined by resilient flexible tube (172) decreases in diameter due to translation of plunger portion (130). In other words, first and second magnets (174, 176) may help ensure resilient flexible tube (172) remains fully encompassed around LES (6) such that resilient flexible tube (172) may suitable engage the outer diameter of LES (6) during exemplary use.

Additionally, a distal end of support collar (138) abuts against a proximal end of auto-tensioning feature (166). As mentioned above, auto-tensioning feature (166) also abuts against spacer tube (168) of exterior sheath (162), such that spacer tube (168) acts as a mechanical ground for auto-tensioning feature (166). Therefore, auto-tensioning feature (166) may compress and expand based on the distance defined by spacer tube (168) of exterior sheath (162) and support collar (138) of plunger portion (130). In particular, auto-tensioning feature (166) is configured to bias plunger portion (130) proximally relative to grip portion (110) of handle assembly (102). Because plunger portion (130) is slidably coupled to grip portion (110) and exterior sheath (162), the biasing force provided by auto-tensioning feature (166) may actuate plunger portion (130) and translating interior shaft (164) in the proximal direction relative to both grip portion (110) and exterior sheath (162).

An operator may actuate plunger portion (130) distally relative to grip portion (110) toward the distal position (as shown in FIGS. 5-6, 19A, and 20A), which in turn compresses auto-tensioning feature (166) between spacer tube (168) and support collar (138). The operator may hold plunger portion (130) in the distal position by overcoming the biasing force of auto-tensioning feature (166) manually or by utilizing locking clip (150).

Locking clip (150) includes a first leg (152) and a second leg (154) that are configured to flex toward and away from each other. Each leg (152, 154) includes a respective locking protrusion (156, 158). As best seen in FIG. 6, legs (152, 154) are dimensioned to rest against a plunger portion (130) such that locking protrusions (156, 158) are housed within locking recesses (135) while plunger portion (130) is in the distal position. Additionally, a proximally facing surface of locking clip (150) simultaneously abuts against a distal face of proximal sleeve (114). Therefore, locking clip (150) may selectively keep plunger portion (130) in the distal position when locking protrusions (156, 158) are received within locking recesses (135). When desired, the operator may manually release plunger portion (130) or remove locking clip (150) such that auto-tensioning feature (166) drives plunger portion (130) and translating interior shaft (164) proximally. In other words, auto-tensioning feature (166) may drive plunger portion (130), interior shaft (164), and resilient flexible tube (172) in order to selectively decrease the dimensions of the loop defined by resilient flexible tube (172).

In the current example, auto-tensioning feature (166) includes a compressed coil spring associated with shaft assembly (160) and is used to bias plunger portion (130) in the proximal direction relative to grip portion (110). However, auto-tensioning feature (166) may be associated with other portions of instrument (100), such as handle assembly (102); and may include any other suitable kind of biasing structure that may be used to proximally bias plunger portion (130) as would be apparent to one having ordinary skill in the art in view of the teachings herein.

For instance, as one merely illustrative variation, a torsional spring and rotating gear may be rotatably coupled to grip portion (110), while a rack may be attached to plunger portion (130) such that the rack meshes with the rotating gear. Such a torsional spring may bias the rotating gear to a first angular position associated with plunger portion (130) being in a completely proximal position. The operator may push plunger portion (130) distally such that the rack of plunger portion (130) rotates the gear and the torsional spring to a second angular position associated with plunger portion (130) in a completely distal position. The operator may release plunger portion (130) such that the torsional spring drives the rotating gear, which in turn drives the rack and plunger portion (130) such that end effector (170) properly engages LES (6) in accordance with the description herein. Attentively, a torsional spring may be incorporated with any other suitable mechanisms utilized to convert angular motion into linear motion that would be apparent to one having ordinary skill in the art in view of the teachings herein, such as a threaded relationship, a camming relationship, etc. As yet another merely illustrative variation, one or more leaf springs or compressible fluid bladders may be used to resiliently bias plunger portion (130) proximally relative to exterior sheath (162). Still other variations will be apparent to those of ordinary skill in the art in view of the teachings herein.

FIGS. 18A-20B show an exemplary use of laparoscopic sizing instrument (100). First, as shown in FIG. 18A, an operator may insert end effector (170) and a distal portion of shaft assembly (160) into a patient laparoscopically such that resilient flexible tube (172) is adjacent to LES (6). FIGS. 19A and 20A show handle assembly (102) corresponding with end effector (170) shown in FIG. 18A. During initial insertion of end effector (170) into the patient, flexible tube (172) may be deformed to a straight configuration in order to enable flexible tube (172) to freely pass through a cannula of a trocar or some other passageway through the patient. By way of example only, plunger portion (130) and interior shaft (164) may be in a proximal-most position, with flexible tube (172) contained within exterior sheath (162), and with a proximal edge of distal tip (178) abutting a distal edge of distal end (165), while end effector (170) is being inserted into the patient. As another merely illustrative example, the operator may grasp flexible tube (172) and substantially straighten flexible tube (172) to assist in feeding flexible tube (172) through a passageway, without necessarily retracting plunger portion (130) and interior shaft (164) to a proximal-most position while inserting end effector (170) into the patient.

Figure 19A:
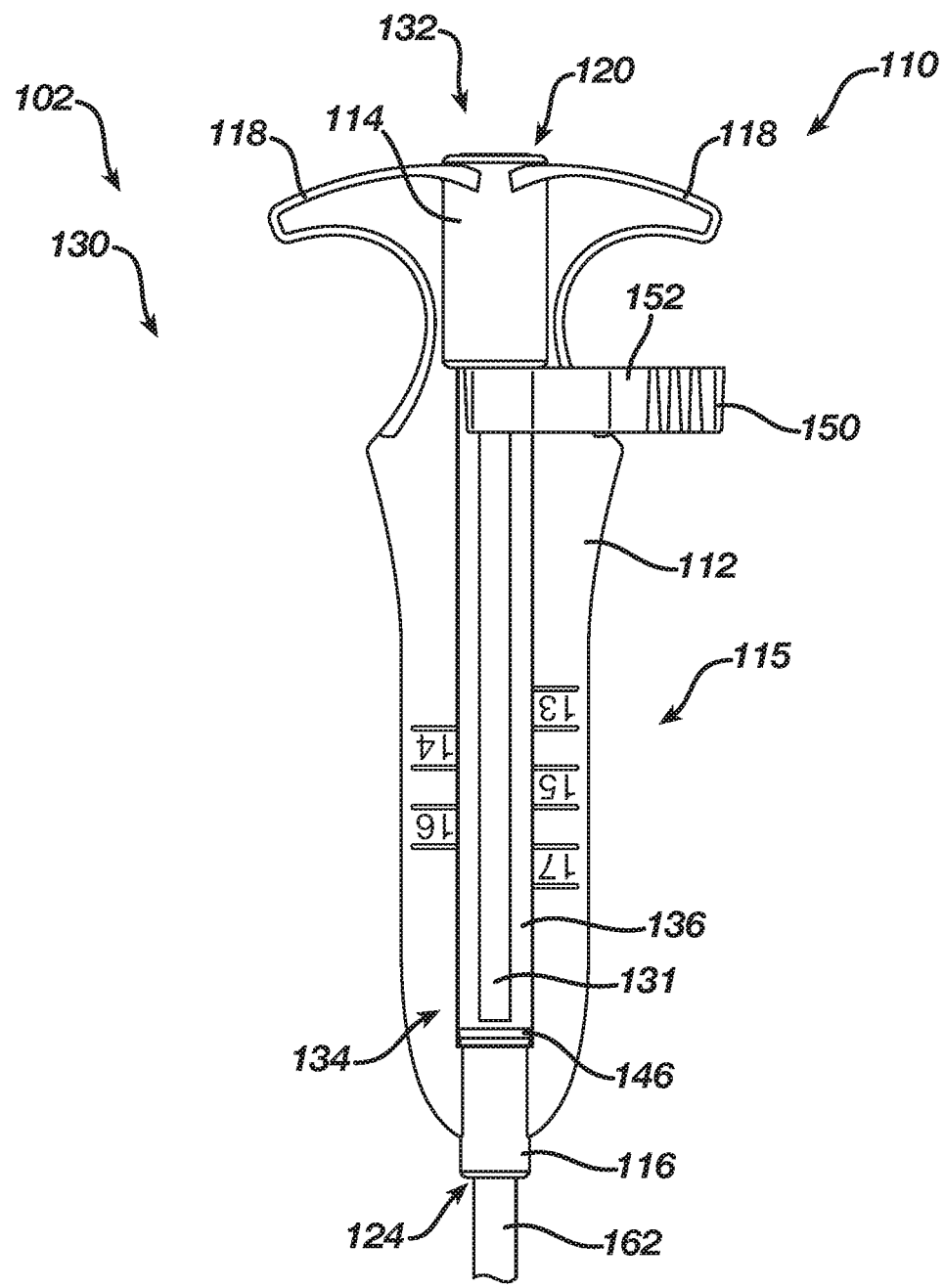
FIG. 19A depicts a top plan view of the handle assembly of FIG. 5, where the plunger portion of FIG. 12 is in a distal position corresponding with the end effector in the distal, closed, position.
Figure 19B:
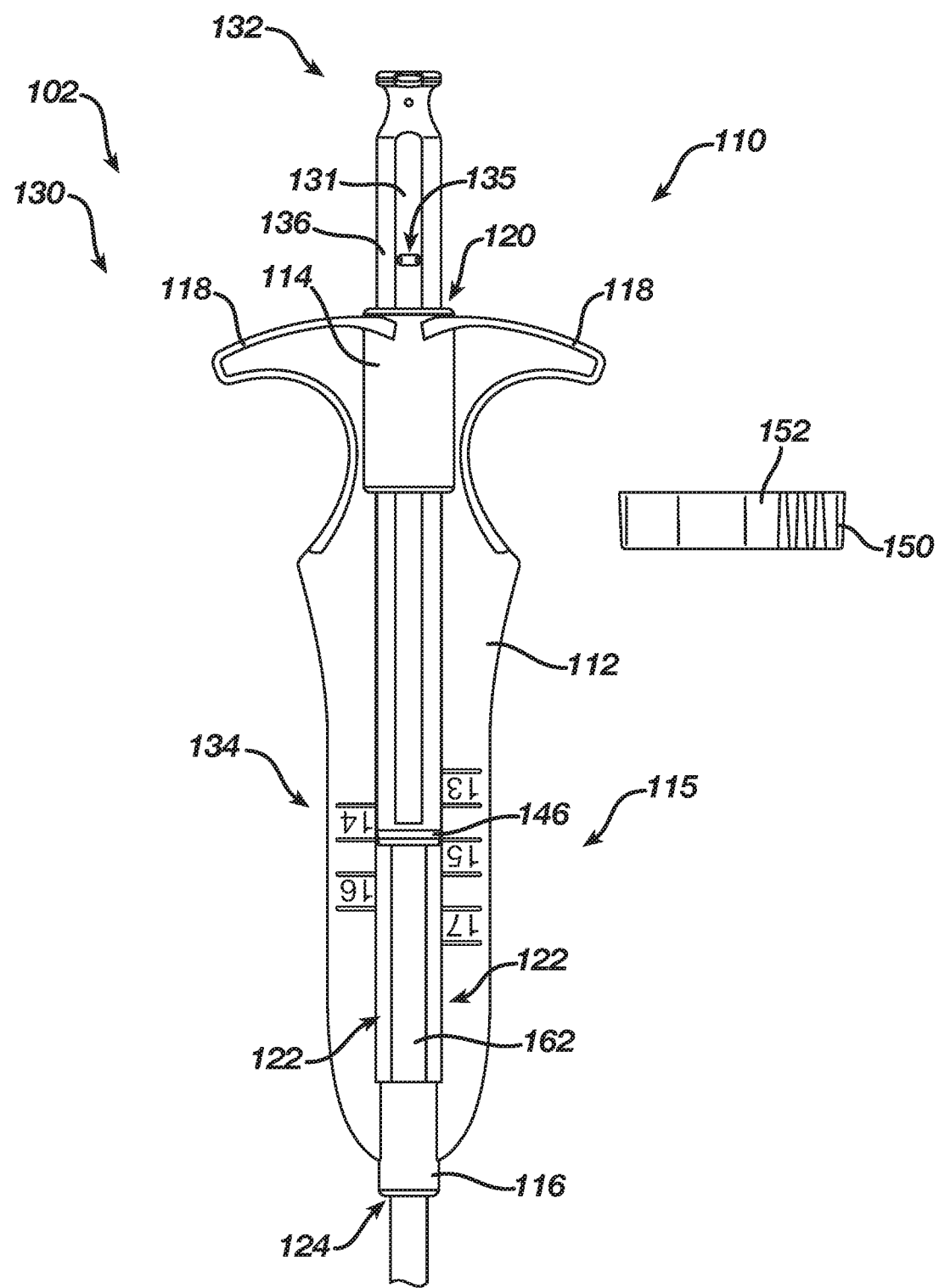
FIG. 19B depicts a top plan view of the handle assembly of FIG. 5, where the plunger portion of FIG. 12 is in a proximal position corresponding with the end effector in the retracted, closed, position.

As shown in FIG. 18A, after end effector (170) has been inserted into the patient, end effector (170) is positioned near the LES (6). As shown, resilient flexible tube (172) is in a closed position corresponding with plunger portion (130) located at the distal position at this stage. Therefore, as mentioned above, with plunger portion (130) at the distal position, resilient flexible tube (172) forms the largest loop. As best shown in FIGS. 19A and 20A, the proximal bias force of auto-tensioning feature (166) is overcome by utilizing locking clip (150) in accordance with the description above. Of course, the operator may also manually hold plunger portion (130) in the distal position to overcome the proximal bias force of auto-tensioning feature (166). To the extent that plunger portion (130) and interior shaft (164) were moved to a proximal-most position while inserting end effector (170) into the patient, plunger portion (130) may be advanced distally relative to grip portion (110) in order to achieve the configuration shown in FIG. 18A.

Next, as shown in FIG. 18B, the operator may grasp and pull a portion of resilient flexible tube (172) in order to overcome the biasing force of both tube (172) and magnets (174, 176) to transition resilient flexible tube (172) from the closed position to the opened position. In the present example, the operator may use a conventional grasping instrument (50) to pull tube (172) into the opened position. Alternatively, any other suitable instrument may be used as would be apparent to one having ordinary skill in the art in view of the teachings herein. With resilient flexible tube (172) in the opened position, the operator may adjust the position of end effector (170) such that LES (6) is next to open distal end (165) of exterior sheath (162). At this stage, handle assembly (102) is still in the position shown in FIGS. 19A and 20A.

Next, as shown in FIG. 18C, the operator may release resilient flexible tube (172) from grasping instrument (50), such that tube (172) resiliently returns to the closed position. At this point, LES (6) is encompassed by resilient flexible tube (172). At this stage, handle assembly (102) is still in the position shown in FIGS. 19A and 20A. Therefore, plunger portion (130) is still in the distal position such that the loop defined by tube (172) is still at its largest dimension. At this point, tube (172) is not suitably engaged with LES (6) to measure the outer diameter of LES (6).

With resilient flexible tube (172) properly encompassing LES (6) in the closed position, the operator may pull locking clip (150) away from the rest of handle assembly (102). With locking clip (150) no longer engaged between plunger portion (130) and grip portion (110), the proximal bias force of auto-tensioning feature (166) drives plunger portion (130) proximally, thereby translating interior haft (164) and resilient flexible tube (172) proximally until tube (172) suitably engages the outer diameter of LES (6). With resilient flexible tube (172) suitably engaging LES (6), plunger portion (130) will remain stationary relative to grip portion (110). At this point in time, the operator may visually confirm the location of indicator (146) relative to indicator markings (115) in order to determine the proper size for an exemplary implant. In the current example, indictor (146) is within the range of a size "14" implant.

It should be understood that auto-tensioning feature (166) may have a spring constant that is large enough to sufficiently drive plunger portion (130) proximally so that flexible tube (172) may suitably engage LES (6); yet weak enough such that once resilient flexible tube (172) sufficiently engages LES (6), the magnetic attraction between magnets (174, 176) keeping tube (172) closed does not break and LES (6) does not deform. In other words, auto-tensioning feature (160) has a spring constant within the acceptable range such that flexible tube (172) properly engages LES (6) without deforming LES (6) or disengaging magnets (174, 176). Auto-tensioning feature (166) may include a spring constant that provides a substantially consistent force against plunger portion (130) during the active length in which auto-tensioning feature (166) drives plunger portion (130). For instance, the output force provided by auto-tensioning feature (166) may deviate by around 5% from when plunger portion (130) is in the most distal position as compared to plunger portion (130) in the most proximal position. Of course, any suitable deviation in output force provided by auto-tensioning feature (166) may be used as would be apparent to one having ordinary skill in the art in view of the teachings herein.

With the suitable measurement of the LES (6) attained, the operator may remove instrument (100) from the patient through any suitable technique that would be apparent to one having ordinary skill in view of the teachings herein. For example, the operator may push plunger portion (130) back into the distal position, use conventional grasping instrument (50) to grasp tube (172) into the opened position, dissociate tube (172) from LES (6), and then remove instrument (100) from patient. Alternatively, the operator may pull plunger portion (130) to the proximal-most position, thereby fully retracting flexible tube (172) into exterior sheath (162) to the point where a proximal edge of distal tip (178) abuts a distal edge of distal end (165). The operator may utilize the measurement of the LES (6) to select an implant that is most appropriate for the patient at hand, to modify an implant so that the implant is at the most appropriate configuration for the patient at hand, and/or for any other purposes.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a handle assembly, wherein the handle assembly comprises: (i) a handle body, and (ii) a plunger portion slidably coupled with the handle body; (b) a shaft assembly extending distally from the handle assembly, wherein the shaft assembly comprises: (i) an external sheath fixed to the handle body, and (ii) an interior shaft coupled to the plunger portion, wherein the interior shaft is slidable relative to the external sheath; (c) an end effector configured to encompass a bodily lumen, wherein the end effector comprises: (i) a flexible member comprising a distal tip, wherein the flexible member extends distally from the interior shaft, (ii) a first coupling element fixed to the distal tip of the flexible member, and (iii) a second coupling element fixed to the external sheath, wherein the first and second coupling elements are configured to be magnetically attracted to each other, wherein the first and second coupling elements are biased toward each other such that the flexible member defines an adjustable loop; and (d) an auto-tensioning feature configured to bias the plunger portion proximally relative to the handle body.

Example 2

The apparatus of Example 1, wherein the handle body comprises a plurality of indicator markings.

Example 3

The apparatus of Example 2, wherein the plunger portion comprises an indicating feature.

Example 4

The apparatus of any one or more of Examples 1 through 3, wherein the plunger portion defines a locking recess.

Example 5

The apparatus of Example 4, wherein the handle assembly further comprises a locking clip, wherein the locking clip is configured mate with the locking recess of the plunger portion when the plunger portion is in a distal position.

Example 6

The apparatus of any one or more of Examples 1 through 5, wherein the handle body defines proximal sleeve, wherein the plunger portion is slidably coupled within the proximal sleeve.

Example 7

The apparatus of Example 6, wherein the proximal sleeve comprises a first flat surface, wherein the plunger portion comprises a second flat surface, wherein the first flat surface and the second flat surface are configured to mate with each other to rotationally lock the plunger portion relative to the handle assembly.

Example 8

The apparatus of any one or more of Examples 1 through 7, wherein the plunger portion comprises an external plunger body and a support collar fixed within the external plunger body, wherein the interior shaft is fixed to the support collar.

Example 9

The apparatus of any one or more of Examples 1 through 8, wherein the auto-tensioning feature comprises a spring.

Example 10

The apparatus of Example 9, wherein the spring is housed within the external sheath of the shaft assembly.

Example 11

The apparatus of Example 10, wherein the external sheath comprises a spacer tube, wherein the spring abuts against the spacer tube.

Example 12

The apparatus of Example 11, wherein the plunger portion defines a distal opening, wherein a portion of the spring extends into the distal opening.

Example 13

The apparatus of any one or more of Examples 1 through 12, wherein the flexible member comprises a resilient tube.

Example 14

The apparatus of Example 13, wherein the resilient tube is biased to define the adjustable loop.

Example 15

The apparatus of any one or more of Examples 1 through 14, wherein the handle assembly comprises a locking collar, wherein the external sheath is fixed to the locking collar.

Example 16

The apparatus of any one or more of Examples 1 through 15, wherein the first coupling element comprises a magnet.

Example 17

An apparatus, the apparatus comprising: (a) a handle assembly, wherein the handle assembly comprises: (i) a handle body, and (ii) a plunger portion slidably coupled with the handle body; (b) a shaft assembly extending distally from the handle assembly, wherein the shaft assembly comprises: (i) an external sheath fixed to the handle body, and (ii) an interior shaft coupled to the plunger portion, wherein the interior shaft is slidable relative to the external sheath; (c) an end effector configured to encompass a bodily lumen, wherein the end effector comprises a flexible member comprising a distal tip, wherein the flexible member extends distally from the interior shaft, wherein the flexible member is biased to define an adjustable loop; and (d) an auto-tensioning feature positioned within the external sheath and around the interior shaft, wherein the auto-tensioning feature is configured to bias the plunger portion proximally relative to the handle body to reduce the adjustable loop defined by the flexible member.

Example 18

The apparatus of Example 17, wherein the plunger portion is rotationally fixed relative to the handle body.

Example 19

The apparatus of any one or more of Examples 17 through 18, wherein the external sheath comprises a spacer tube, wherein the auto-tensioning feature abuts against the spacer tube.

Example 20

An apparatus, the apparatus comprising: (a) a handle assembly, wherein the handle assembly comprises: (i) a static body, and (ii) an actuating body slidably coupled with the static body; (b) a shaft assembly extending distally from the handle assembly, wherein the shaft assembly comprises: (i) an external sheath fixed to the static body, wherein the external sheath defines a distal opening, and (ii) an interior shaft fixed to the actuating body; (c) an end effector configured to encompass a bodily lumen, wherein the end effector comprises a flexible member attached to the interior shaft, wherein a distal portion of the flexible member extends distally past the distal opening of the external sheath, wherein the distal portion of the flexible member is biased to form an adjustable loop; and (d) an auto-tensioning feature configured to bias the actuating body portion proximally relative to the static body.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a handle assembly, wherein the handle assembly comprises:
      (i) a handle body, and
      (ii) a plunger portion slidably coupled with the handle body;
   (b) a shaft assembly extending distally from the handle assembly, wherein the shaft assembly comprises:
      (i) an external sheath fixed to the handle body, and
      (ii) an interior shaft coupled to the plunger portion, wherein the interior shaft is slidable relative to the external sheath;
   (c) an end effector configured to encompass a bodily lumen, wherein the end effector comprises:
      (i) a flexible member comprising a distal tip, wherein the flexible member extends distally from the interior shaft,
      (ii) a first coupling element fixed to the distal tip of the flexible member, and
      (iii) a second coupling element fixed to the external sheath, wherein the first and second coupling elements are configured to be magnetically attracted to each other, wherein the first and second coupling elements are biased toward each other such that the flexible member defines an adjustable loop; and
   (d) an auto-tensioning feature configured to bias the plunger portion proximally relative to the handle body.

2. The apparatus of claim 1, wherein the handle body comprises a plurality of indicator markings.

3. The apparatus of claim 2, wherein the plunger portion comprises an indicating feature.

4. The apparatus of claim 1, wherein the plunger portion defines a locking recess.

5. The apparatus of claim 4, wherein the handle assembly further comprises a locking clip, wherein the locking clip is configured mate with the locking recess of the plunger portion when the plunger portion is in a distal position.

6. The apparatus of claim 1, wherein the handle body defines proximal sleeve, wherein the plunger portion is slidably coupled within the proximal sleeve.

7. The apparatus of claim 6, wherein the proximal sleeve comprises a first flat surface, wherein the plunger portion comprises a second flat surface, wherein the first flat surface and the second flat surface are configured to mate with each other to rotationally lock the plunger portion relative to the handle assembly.

8. The apparatus of claim 1, wherein the plunger portion comprises an external plunger body and a support collar fixed within the external plunger body, wherein the interior shaft is fixed to the support collar.

9. The apparatus of claim 1, wherein the auto-tensioning feature comprises a spring.

10. The apparatus of claim 9, wherein the spring is housed within the external sheath of the shaft assembly.

11. The apparatus of claim 10, wherein the external sheath comprises a spacer tube, wherein the spring abuts against the spacer tube.

12. The apparatus of claim 11, wherein the plunger portion defines a distal opening, wherein a portion of the spring extends into the distal opening.

13. The apparatus of claim 1, wherein the flexible member comprises a resilient tube.

14. The apparatus of claim 13, wherein the resilient tube is biased to define the adjustable loop.

15. The apparatus of claim 1, wherein the handle assembly comprises a locking collar, wherein the external sheath is fixed to the locking collar.

16. The apparatus of claim 1, wherein the first coupling element comprises a magnet.

17. An apparatus, the apparatus comprising:
(a) a handle assembly, wherein the handle assembly comprises:
   (i) a handle body, and
   (ii) a plunger portion slidably coupled with the handle body;
(b) a shaft assembly extending distally from the handle assembly, wherein the shaft assembly comprises:
   (i) an external sheath fixed to the handle body, and
   (ii) an interior shaft coupled to the plunger portion, wherein the interior shaft is slidable relative to the external sheath;
(c) an end effector configured to encompass a bodily lumen, wherein the end effector comprises a flexible member comprising a distal tip, wherein the flexible member extends distally from the interior shaft, wherein the flexible member is biased to define an adjustable loop; and
(d) an auto-tensioning feature positioned within the external sheath and around the interior shaft, wherein the auto-tensioning feature is configured to bias the plunger portion proximally relative to the handle body to reduce the adjustable loop defined by the flexible member.

18. The apparatus of claim 17, wherein the plunger portion is rotationally fixed relative to the handle body.

19. The apparatus of claim 17, wherein the external sheath comprises a spacer tube, wherein the auto-tensioning feature abuts against the spacer tube.

20. An apparatus, the apparatus comprising:
(a) a handle assembly, wherein the handle assembly comprises:
   (i) a static body, and
   (ii) an actuating body slidably coupled with the static body;
(b) a shaft assembly extending distally from the handle assembly, wherein the shaft assembly comprises:
   (i) an external sheath fixed against movement relative to the static body, wherein the external sheath defines a distal opening, and
   (ii) an interior shaft fixed against movement relative to the actuating body, wherein the interior shaft includes a distal end;
(c) an end effector configured to encompass a bodily lumen, wherein the end effector comprises a flexible member attached to the interior shaft and having a proximal end, wherein the proximal end of the flexible member is fixed against movement relative to the distal end of the interior shaft, wherein a distal portion of the flexible member extends distally past the distal opening of the external sheath, wherein the distal portion of the flexible member is biased to form an adjustable loop; and
(d) an auto-tensioning feature configured to bias the actuating body proximally relative to the static body.

* * * * *